(12) United States Patent
Alexander et al.

(10) Patent No.: US 10,842,602 B2
(45) Date of Patent: Nov. 24, 2020

(54) TOOLS AND METHODS FOR TREATMENT OF PELVIC CONDITIONS

(71) Applicant: Boston Scientific Scimed, Inc., Maple Grove, MN (US)

(72) Inventors: James A. Alexander, Excelsior, MN (US); Benjamin Y. Arcand, Minneapolis, MN (US); Kevin R. Arnal, Excelsior, MN (US); Dean W. Hacker, Maple Grove, MN (US); Karl Alan Jagger, Deephaven, MN (US); Chaouki A. Khamis, Cupertino, CA (US); Jelica D. Wold, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 123 days.

(21) Appl. No.: 15/989,928

(22) Filed: May 25, 2018

(65) Prior Publication Data
US 2018/0271634 A1 Sep. 27, 2018

Related U.S. Application Data

(63) Continuation of application No. 14/434,670, filed as application No. PCT/US2013/065253 on Oct. 16, 2013, now Pat. No. 9,993,323.
(Continued)

(51) Int. Cl.
*A61F 2/00* (2006.01)
*A61B 17/068* (2006.01)
(Continued)

(52) U.S. Cl.
CPC .......... *A61F 2/0045* (2013.01); *A61B 17/068* (2013.01); *A61B 17/3468* (2013.01);
(Continued)

(58) Field of Classification Search
CPC .................. A61F 2/0045; A61F 2/0063; A61F 2230/006; A61F 2230/0097;
(Continued)

(56) References Cited

U.S. PATENT DOCUMENTS 4,424,311 A  1/1984  Nagaoka et al.
5,474,915 A  12/1995  Dordick et al.
(Continued)

FOREIGN PATENT DOCUMENTS

WO  2011082350 A1  7/2011

OTHER PUBLICATIONS

First Examination Report for Australian Application 2013331359, dated Apr. 28, 2017, 4 pages.

*Primary Examiner* — Thaddeus B Cox
(74) *Attorney, Agent, or Firm* — Brake Hughes Bellermann LLP

(57) ABSTRACT

Described are implants and dilators useful in a sacral colpopexy procedure, and related methods. The present invention relates to systems, tools, and methods for treating pelvic organ prolapse by use of a pelvic implant to support pelvic tissue. The pelvic treatments include, for example, treatment of vaginal prolapse by laparoscopic or abdominal procedures.

19 Claims, 12 Drawing Sheets

Related U.S. Application Data

(60) Provisional application No. 61/714,500, filed on Oct. 16, 2012, provisional application No. 61/726,341, filed on Nov. 14, 2012.

(51) Int. Cl.
    *A61L 27/06*    (2006.01)
    *A61L 27/14*    (2006.01)
    *A61L 27/22*    (2006.01)
    *A61L 27/28*    (2006.01)
    *A61B 17/34*    (2006.01)
    *A61M 29/00*    (2006.01)
    *A61B 17/00*    (2006.01)

(52) U.S. Cl.
    CPC .............. *A61L 27/06* (2013.01); *A61L 27/14* (2013.01); *A61L 27/225* (2013.01); *A61L 27/28* (2013.01); *A61M 29/00* (2013.01); *A61B 2017/00876* (2013.01); *A61F 2/0063* (2013.01); *A61F 2210/0014* (2013.01); *A61F 2220/0016* (2013.01); *A61F 2230/006* (2013.01); *A61F 2240/004* (2013.01); *A61F 2250/0097* (2013.01); *A61L 2400/16* (2013.01)

(58) Field of Classification Search
    CPC .. A61F 2017/00805; A61F 2017/00876; A61F 2/0031–0045; A61F 2002/0068–0072
    See application file for complete search history.

(56) References Cited

U.S. PATENT DOCUMENTS

| | | |
|---|---|---|
| 2002/0028980 A1 | 3/2002 | Thierfelder et al. |
| 2003/0100108 A1 | 5/2003 | Altman et al. |
| 2005/0277811 A1 | 12/2005 | Richards et al. |
| 2005/0283189 A1 | 12/2005 | Rosenblatt |
| 2009/0248071 A1 | 10/2009 | Saint et al. |
| 2010/0081865 A1 | 4/2010 | Hamati |
| 2010/0280309 A1 | 11/2010 | Von Pechmann |
| 2010/0305394 A1 | 12/2010 | Rosenblatt |
| 2011/0052695 A1 | 3/2011 | Jiang et al. |
| 2011/0124956 A1 | 5/2011 | Mujwid et al. |
| 2011/0144417 A1 | 6/2011 | Jagger et al. |
| 2011/0174313 A1 | 7/2011 | Von Pechmann et al. |
| 2012/0016185 A1 | 1/2012 | Sherts et al. |
| 2012/0022318 A1 | 1/2012 | Thierfelder et al. |
| 2012/0253107 A1* | 10/2012 | Gindele ................ A61F 2/0045 600/30 |
| 2013/0197537 A1 | 8/2013 | Fairneny et al. |

* cited by examiner

TOOLS AND METHODS FOR TREATMENT OF PELVIC CONDITIONS

STATEMENT OF PRIORITY

This application is a continuation of U.S. patent application Ser. No. 14/434,670, filed on Apr. 9, 2015, now U.S. Pat. No. 9,993,323, which is a U.S. national stage application under 35 U.S.C. 371 of International Application No. PCT/US2013/065253, which was granted an International Filing Date of Oct. 16, 2013, which in turn claims the benefit of U.S. Provisional Patent Application Ser. No. 61/714,500, filed Oct. 16, 2012, entitled "TOOLS AND METHODS FOR TREATMENT OF PELVIC CONDITIONS", and U.S. Provisional Patent Application Ser. No. 61/726,341, filed Nov. 14, 2012, entitled "TOOLS AND METHODS FOR TREATMENT OF PELVIC CONDITIONS", the disclosures of which are incorporated herein by reference in their entireties.

FIELD OF THE INVENTION

The present invention relates to systems, tools, and methods for treating pelvic organ prolapse by use of a pelvic implant to support pelvic tissue. The pelvic treatments include, for example, treatment of vaginal prolapse by laparoscopic or abdominal procedures.

BACKGROUND

Pelvic health for women is a medical area of increasing importance, at least in part due to an aging population. Examples of common pelvic ailments include incontinence (e.g., fecal and urinary incontinence), pelvic tissue prolapse (e.g., female vaginal prolapse), and other conditions that affect the pelvic floor. Pelvic disorders such as these can be caused by weakness or damage to normal pelvic support systems. Common etiologies include childbearing, removal of the uterus, connective tissue defects, prolonged heavy physical labor, and postmenopausal atrophy.

Pelvic floor disorders include cystocele, rectocele, and prolapse such as anal, uterine, and pelvic organ prolapse. Pelvic organ prolapse is a condition that occurs when the upper portion of the vagina loses its normal shape and moves downwardly into the vaginal canal. In its severest forms, pelvic organ prolapse can result in the distension of the vaginal apex outside of the vagina. Pelvic organ prolapse may occur alone, such as can be caused by weakness of the pelvic and vaginal tissues and muscles, or can be associated with a rectocele, cystocele and/or enterocele. Prolapse can represent a challenge for surgeons to treat. Some of these treatments include, for example, abdominal sacralcolpopexy (SCP), which may be performed laparoscopically, and transvaginal sacralcolpopexy (TSCP), wherein these procedures are performed using a variety of different instruments, implants, and surgical methods. It is known to repair pelvic organ prolapse by suturing the vaginal vault (e.g., by stitches) to the supraspinous ligament or by attaching the vaginal vault through mesh or fascia to the sacrum.

There is ongoing need to provide physicians with improved methods and associated systems, tools, and implants for treating pelvic conditions such as pelvic organ prolapse, wherein such methods can include those that are minimally invasive, safe, and highly effective.

SUMMARY

Systems, tools, and methods as described herein can be used to treat pelvic conditions such as vaginal prolapse caused by muscle and ligament weakness, hysterectomies, and the like. In accordance with the invention, sacral colpopexy procedures can be performed through an abdominal opening, laparoscopically, or transvaginally, each of which may require different approaches, which can use certain embodiments of systems or methods of the invention. An implant or other tool described herein as useful in a laparoscopic procedure, to access tissue at an outside surface of a vagina at a surgical site at a pelvic region of a patient (e.g., to deliver an implant, fastener (staple, suture, adhesive, grommet, etc.), or other surgical item), can exhibit a cross-sectional diameter that is able to pass through a laparoscopic trocar, such as a cross sectional diameter that is less than 1 centimeter, e.g., less than 8, millimeters, or less than 6 millimeters.

In a sacral colpopexy procedure it is desirable to simplify the process of attaching an implant within a patient using implantation tools and fasteners having various features. Implants can include those that are Y-shaped, which include a base member and two support members extending from the base member, wherein the attachment of portions of the Y-shaped implant can be adjustable relative to their respective attachment points within a patient (e.g., the sacrum). Additionally, a Y-shaped implant can include at least two pieces (an extension portion or a support portion) that engage with each other.

Systems described herein relate to systems and methods to aid in implantation of a pelvic implant, specifically a Y-sling. Certain embodiments of methods and implants described herein involve the use of a Y-shaped sling that is designed to fixate to the sacral promontory, and may additionally include two apical mesh pieces that are sutured to the anterior and posterior vaginal walls. Embodiments of implants and methods can involve placement of an implant to support pelvic tissue by way of an incision of minimum size.

Certain embodiments relate generally to fixation of the Y-shaped sling and related means for fixing the pelvic implant to the vagina for the treating of pelvic organ prolapse. Embodiments of the system can include an implant having a tissue support portion and one or more extension portions, fasteners, and a dilator. Optionally, the systems may include a deployment tool for inserting the implant into the patient and an attachment tool for aiding in implantable of the fasteners.

In one aspect the invention relates to a system for performing sacral colpopexy in a female patient, the system including a Y-sling implant and a dilator. The dilator can include a distal end adapted to pass through a vaginal introitus to place the distal end within a vagina of the patient and a proximal end that is external to the patient with the distal end placed within the vagina.

In another aspect the invention relates to a method of performing a sacral colpopexy. The method includes: providing a system as described herein, such as at any of claims 1 through 18; passing a distal end of the dilator through a vaginal introitus and positioning the distal end within a vagina of the patient, and using the proximal end to manipulate the distal end to support vaginal tissue; passing the Y-sling into the patient through an abdominal incision or a laparoscopic incision to place the Y-sling at a location of outside vaginal tissue; placing a vaginal leaf of the Y-sling at outside vaginal tissue and fastening the vaginal leaf to the vaginal tissue; and fastening a sacral leaf of the Y-sling to tissue at a region of sacral anatomy.

In another aspect the invention relates to a dilator adapted to support vaginal tissue by being passed through a vaginal introitus and being located at an interior of a vagina. The dilator includes a distal end adapted to pass through the vaginal introitus to place the distal end within the vagina, and a proximal end that is external to the patient with the distal end placed within the vagina. The distal end includes one or any combination of two or more of: a light; an alignment feature that can be identified through the vaginal tissue with the distal end placed within the vagina; a distal end adapted to be expanded and folded about a longitudinal axis; multiple openings in fluid communication with the proximal end, each opening adapted to contact a surface of interior vaginal tissue to expose the surface of interior vaginal tissue to a reduced (vacuum) pressure to maintain contact between the interior vaginal tissue and an outer surface of the distal end.

In yet another aspect the invention relates to a Y-sling capable of being reduced in cross section to a size that can be passed through a laparoscopic trocar. The Y-sling includes a posterior vaginal leaf, an anterior vaginal leaf, and a sacral leaf. The Y-sling additionally includes one or any combination of the following features: one or more of the leafs contains a frame; one or more of the leafs includes adhesive; a connector extending between opposed edges of the vaginal leafs to connect the edges of the vaginal leafs; one or two of the vaginal leafs includes a fastener located on an inner surface of the vaginal leaf, the fastener adapted to pass into vaginal tissue without passing through the vaginal tissue; the Y-sling is molded and includes fenestrations; one or more of the vaginal leafs includes one or more demarcation indicating a location for placing a fastener to secure the leaf to vaginal tissue.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
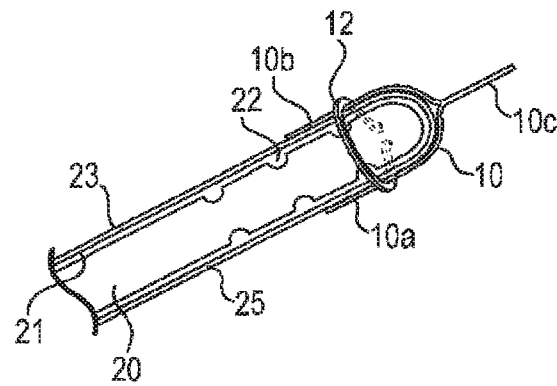
FIG. 1 illustrates a cross sectional view of a vaginal dilator and a fastener.

The methods and tools as described can be useful in procedures for supporting vaginal tissue, such as methods to treat pelvic organ prolapse by a sacral colpopexy procedure, for instance a sacral colpopexy performed laparoscopically. A sacral colpopexy is a procedure for providing vaginal vault (a.k.a., vaginal cuff) suspension. The procedure can include the use of an implant such as a strip of mesh or other material attached between posterior vaginal tissue (e.g., a vaginal cuff) and a region or component of sacral anatomy such as the sacrum (the sacrum bone itself), a nearby sacrospinous ligament, uterosacral ligament, or anterior longitudinal ligament at the sacral promontory. Attachment to the sacral anatomy may be accomplished as desired, e.g., by using a bone screws implanted at the sacrum or by use of an alternate fastener for fastening to soft tissue. Sacral colpopexy may be performed through an abdominal incision, transvaginally, or laparoscopically. In some sacral colpopexy procedures that also involve a hysterectomy, an implant can be attached to posterior vaginal tissue that remains after removal of a uterus and cervix, and also to anatomy to support the vaginal tissue at or around the sacrum, such as to uterosacral ligaments or to the sacrum itself (i.e., to a component of the sacral anatomy).

Devices, systems, and methods as described herein are directed generally to treating pelvic organ prolapse. The system and methods as described can be useful in procedures for placement of a pelvic implant for a sacral colpopexy procedure. Exemplary procedures include laparoscopic or abdominal sacral colpopexy procedures. An exemplary laparoscopic sacral colpopexy procedure includes introducing the implant (i.e., a Y-sling) into the abdomen and using a fastening mechanism (e.g., suture, staple, adhesive, etc.) to attach the implant to the vaginal cuff. A dilator may aid supporting and operating upon the vaginal cuff during such procedure.

In a sacral colpopexy procedure it is desirable to simplify the process of attaching an implant within a patient using implantation tools and fasteners having various features. Useful implants can include known implants referred to sometimes as "Y-mesh" (also "Y-sling") implants that are Y-shaped, including a base member (sacral leaf) and two support members extending from the base member (vaginal leafs). Optionally, portions of the Y-shaped implant can be adjustable relative to their respective attachment points within a patient (e.g., the sacrum). Additionally, a Y-shaped implant can include at least two pieces (an extension portion or a support portion) that engage with each other. Systems described herein relate to systems and methods to aid in implantation of a pelvic implant, such as a Y-sling.

Certain embodiments of methods and implants described herein involve the use of a Y-shaped sling that is designed to fixate to the sacral promontory, and may additionally include two apical mesh pieces (vaginal leafs) that can be attached to vaginal tissue such as at the anterior and posterior vaginal walls, in performing a sacral colpopexy, e.g., laparoscopically. Examples of implants that include features in common with implants that can be useful as described are shown and described in Assignee's co-pending application having U.S. Publication No. 2012/0022318, filed Oct. 4, 2011, by Thierfelder et al., entitled IMPLANTABLE ARTICLE AND METHOD, the entirety of which is incorporated herein by reference.

The present description presents new or improved devices, implants, tools, and systems for placing of a pelvic implant in performing a sacral colpopexy procedure. Exemplary procedures include laparoscopic and trans-abdominal sacral colpopexy procedures. An exemplary laparoscopic sacral colpopexy procedure includes introducing the implant (i.e., a Y-sling) into the abdomen laparoscopically, and using a fastening mechanism to attach the implant to the vaginal cuff, also laparoscopically, optionally supporting vaginal tissue and a vaginal cuff by passing a dilator through a vaginal introitus to be located within the vagina interior during the procedure. The dilator can support the vaginal tissue internally and can be manipulated by a handle at a proximal end of the dilator that extends to a location external to the vagina.

Certain of the useful devices as described can be generally referred as a vaginal dilator (or manipulator). A dilator is a device adapted to be placed within a vagina, internally, to support vaginal tissue internally, while an abdominal or laparoscopic surgical procedure is being performed in the vaginal area, such as a sacral colpopexy during which implant material is contacted with and attached to the exterior or outside of the vaginal tissue, meaning the vaginal tissue that is internal to a pelvic region of the patient and accessible surgically through a laparoscopic or abdominal incision. In use, the dilator can be inserted into the patient so that the surgeon can manipulate and support vaginal tissue, especially posterior vaginal tissue, while operating surgically at a site in the pelvic region. The dilator can be disposable or reusable and can be used as described herein, optionally in conjunction with specified other devices or method steps, preferably to reduce surgical time and improve surgical outcomes by aiding in tissue dissection, fastener (e.g., suture) placement, implant (e.g., mesh) placement, etc. The dilator can be made using any useful rigid polymer, such as an inexpensive acrylonitrile butadiene styrene (ABS) or polycarbonate material, or other similar polymers, optionally including such polymers that exhibit effective light conducting properties.

FIG. 1 illustrates a system useful to aid the placement of a pelvic implant for the treatment of vaginal prolapse. In one embodiment, vaginal leafs 10a and 10b of a Y-sling 10 are placed over the vaginal cuff in contact with anterior and posterior vaginal tissue; a sacral leaf 10e extends and is suspended at the peritoneal cavity by attachment to a region of sacral anatomy. As illustrated, dilator 20 is inserted into the vagina to support the vagina during the surgical procedure. A proximal end of dilator 20 (not shown) is external to the patient and can be manipulated to manipulate, approximate, and control vaginal tissue 25. The dilator 20 has one or more alignment mechanism 22 located at a distal end, which become located near a vaginal cuff when placed inside of the vagina (see FIGS. 1 and 2b). The alignment mechanism 22 can be a groove, ridge, channel, notch, bump or other surface structure, indentation, or protrusion that can be identified through vaginal tissue 25 at outer vaginal tissue 23. Alignment mechanism 22 is a structure of sufficient size or form that when dilator 20 is placed within the vagina and in contact with an interior vaginal wall 21, alignment mechanism 22 can be useful to a surgeon having access to outer vaginal tissue 23; a surgeon is capable of identifying alignment mechanism 22 by contacting outer vaginal tissue 23, e.g., with a surgical instrument such as a suture, clip (e.g., 12), or other fastener or fastener placement tool by using the fastener or tool to sense or identify the location of alignment mechanism 22 through the vaginal tissue 25, e.g., and locate a clip 12 at outer vaginal 23 and in alignment with a location of alignment mechanism 22 with dilator 20 installed intra-vaginally. As such, alignment mechanism 22 can be used to place and align a structure such as a fastener (e.g., clip 12) at a location of outer vaginal tissue 23, such as a fastening structure adapted to maintain a position of an implant material (e.g., a leaf 10a or 10b) at a location of outer vaginal tissue 23.

As illustrated at FIG. 1, alignment mechanism 22, which is identifiable through the vaginal tissue 25, aids the physician with placement of fastener 12. Fastener 12 may take the form of a suture, rubberband, elastic band, staple, magnet, clip, clamp or other like device.

An exemplary fastener 12 (as illustrated) may be in the form of a plastic or metal ring or spring clip adapted to be placed at outer vaginal tissue 23, e.g., laparoscopically, in communication with alignment mechanism 22 of dilator 20 by aligning fastener 12 with the alignment mechanism 22. Fastener 12 may be rounded, e.g., circular, C-shaped, or U-shaped, and can be constructed of a spring-like material like that of a clamp, spring, or other similar fastener or device that may be fitted about outer vaginal tissue 23 and leafs 10a and 10b of implant 10 while dilator 20 is located internal to the vagina. In use, fastener 12 fits about outer vaginal tissue 23 and also about mesh portions 10a, 10b of implant 10, as illustrated, e.g., to hold one or two vaginal leafs 10a, 10b of a Y-mesh to anterior and posterior vaginal tissue. Fastener 12 may be made from a plastic, metal, other biocompatible material or combinations thereof.

Figure 2A:
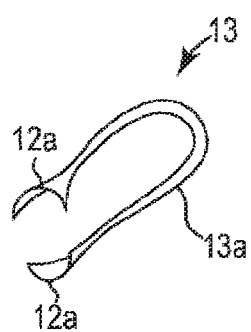
FIGS. 2a and 2b illustrate an alternative fastener.
Figure 2B:
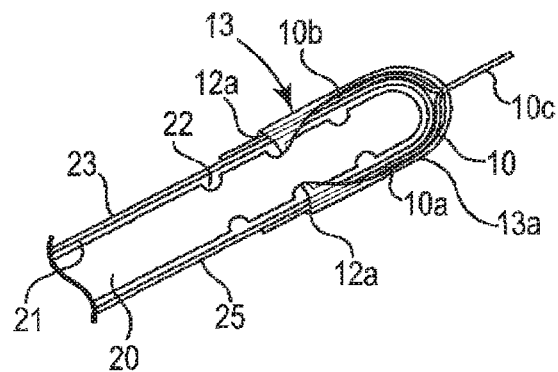

Another example of a fastener can be in the form of opposed fastener 12a illustrated at FIG. 2a, which are part of a larger clip 13. Clip 13 may be in the form of a plastic or metal device as shown at FIG. 2a, including two opposed curved fasteners 12a connected together by curved frame 13a. Frame 13a is adapted to extend over an end of a vaginal cuff and a Y-mesh 10 (see FIG. 1), with curved fasteners 12a adapted to communicate through vaginal tissue with one of alignment mechanisms (e.g., grooves) 22. Opposed fasteners 12a may be rounded, e.g., circular, C-shaped, or U-shaped; frame 13a can be made of a spring-like material like that of a clamp, spring, or other similar device that may be fitted about outer vaginal tissue 23 and over a vaginal cuff with one of fasteners 12a located at posterior tissue of a vaginal cuff and the second fastener 12a being located at anterior tissue of the vaginal cuff, with leafs 10a and 10b in contact with the vaginal tissue, while dilator 20 is located internal to the vagina. In use, fasteners 12a fit about outer vaginal tissue 23, in communication through vaginal tissue with alignment mechanism 22, over a vaginal cuff and in contact with anterior and posterior tissues of the vaginal cuff to maintain leafs 10a, 10b in contact with anterior and posterior vaginal tissue. See FIG. 2b.

While FIG. 1 shows three alignment mechanisms 22 extending continuously about a perimeter of dilator 20 at different locations along a length of dilator 20, more than three or fewer than three may be present. As illustrated, alignment mechanisms 22 are in the form of continuous depressions or grooves extending about an outer perimeter of the shaft of dilator 20; other structures can also be useful, such as continuous or non-continuous rounded or pointed ridges, bumps, or the like, extending about the outer perimeter of the shaft. FIG. 1 also shows only a single fastener 12, but two or more may be useful if desired.

A dilator 20 and fastener 12 or 12a as shown may be particularly useful in performing a laparoscopic sacral colpopexy. According to such a method, dilator 20 may be inserted into a vaginal introitus to locate a shaft of dilator 20 internal to the vagina with one or more alignment mechanism 22 located at a posterior portion of the vagina, e.g., adjacent to the vaginal cuff, and a proximal portion of dilator 20 remaining external to the patient. A surgeon may manipulate the proximal portion of dilator 20 to manipulate, control, or support vaginal tissue (25) near the vaginal cuff, during laparoscopic placement of implant 10 into the patient, during laparoscopic placement of vaginal leafs 10a and 10b of implant 10 at vaginal tissue anterior and posterior to the vaginal cuff, and during laparoscopic placement of one or more fastener 12 or 12a to hold the leafs 10a, 10b of implant 10 in contact with the anterior and posterior tissue of a vaginal cuff. Dilator 20 may be removed after surgery or may optionally remain in the vagina of the patient for a time after the surgery to allow tissue ingrowth at the implant or for a time useful to secure leafs 10a and 10b to the vaginal tissue by an alternate fastening mechanism (a fastener different from fastener 12 or 12a such as a suture, adhesive, staple, etc). Fastener 12 or 12a may be removed after leafs 10a and 10b have been secured to vaginal tissue, e.g., by ingrowth of tissue into Y-mesh 10 or by use of a different fastener to secure leaf 10a or 10b to vaginal tissue. More generally, fastener 12 or 12a may be permanent and need not be removed after placement, may be bioabsorbable, or may be removed (e.g., laparoscopically or trans-abdominally) after tissue ingrowth or placement of an alternate fastener at implant 10.

Figure 2C:
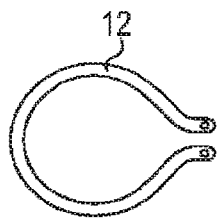
FIG. 2c illustrates a cross sectional view of a fastener as shown at FIG. 1.

FIG. 2c is a top view of fastener 12.

Figure 3A:
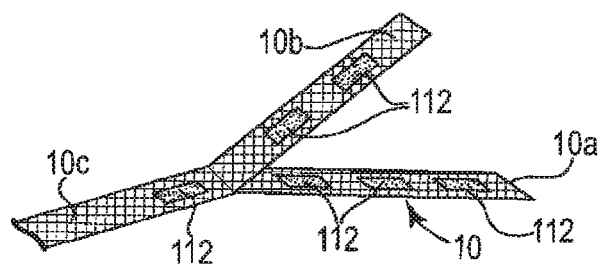
FIGS. 3a (side perspective view) and 3b (top view) illustrate a mesh sling with an adherent.
Figure 3B:
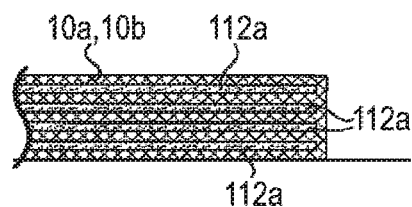
Figure 4A:
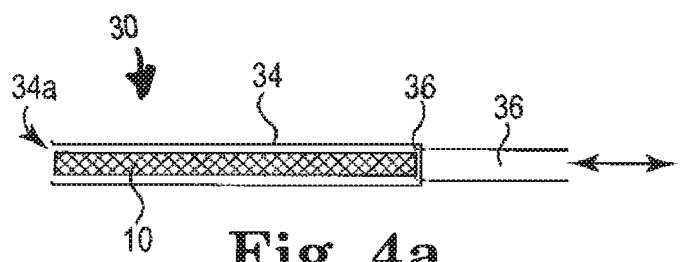
FIGS. 4a, 4b, 4c, and 4d illustrate a sling deployment tool and alternative states during a method of use.
Figure 4B:
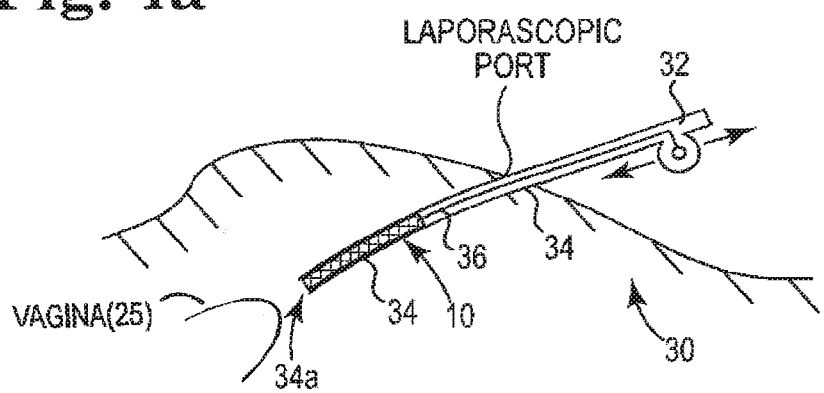
Figure 4C:
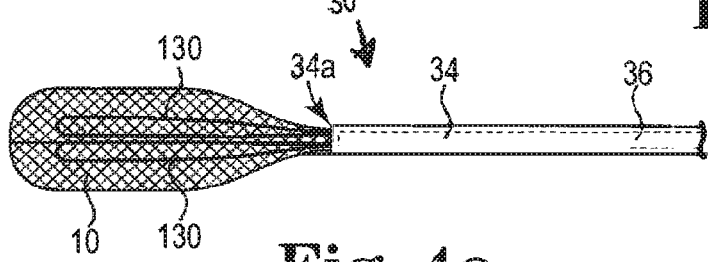
Figure 4D:
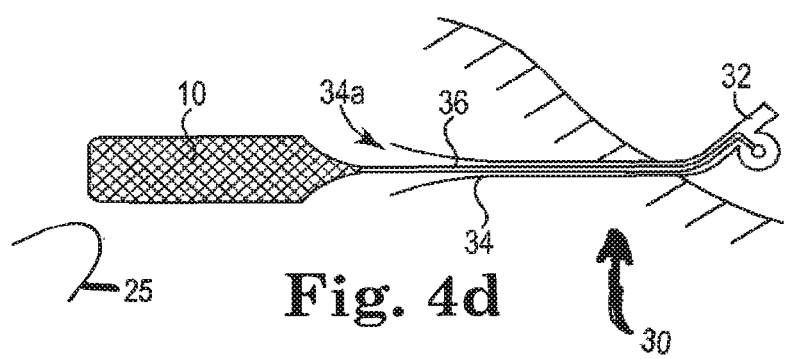

FIGS. 3a and 3b illustrate the use of an adhesive material as a fastener 112 (including 112a) to adhere vaginal leafs 10a and 10b to vaginal tissue (not shown) at locations posterior and anterior to the vaginal cuff. An adhesive material 112 may be placed onto areas of a surface of vaginal leafs 10a and 10b of implant 10 as patches on the Y-sling 10. Alternately, adhesive 112 may be placed over the entire surface of vaginal leafs 10a and 10b of Y-sling 10, or on any amount of the surfaces in-between. The adhesive material 112, 112a may be methylcellulose, hyaluronic acid, or other like materials that become sticky when exposed to moisture or heat. Other biologic adhesives may also be useful, such as those including silk fibroin.

Silk fibroin is the primary structural component of silk, and composed of heavy and light chains monomeric units. Silk fibroin can be obtained from natural materials produced by an organism, such as raw cocoons from a silkworm. Using techniques known in the art, the natural material can be degummed to remove sericin (a gum coating the fibroin fibers) in order to enrich or purify the silk fibroin. Degumming can be performed by treating naturally-occurring fibrous silk with a dissolution or chaotropic agent. For example, as described in U.S. Pub No. 20110052695, dissolved silk can be generated in the presence of lithium bromide at an elevated temperature (e.g., a 4 hour digestion at 60.degree. C. in a 9.3 M aqueous solution of lithium bromide to provide purified silk fibroin at a concentration of about 200 g/L). This treatment can provide uniformly and repeatably dissociated silk fibroin molecules to ensure similar fibroin solution properties. Methods for performing sericin extraction have also been described in U.S. Publication No. 2003/0100108 and Meesilpa, P., (2002) The Sericulture Research Institute, Annual Research Reports, 165-172.

An adhesive with silk fibroin can also include a hydrogel-forming material. The hydrogel-forming material can be a crosslinkable compound, such as a crosslinkable small molecule, oligomer, or polymer having two or more crosslinkable groups. Exemplary crosslinkable groups include free radically polymerizable groups such as acrylates and methacrylates. Examples of polymerizable small molecules include trimethylolpropane triacrylate, trimethylolpropane trimethacrylate, trimethylol propane tetraacrylate, monosaccharide acrylates, oligosaccharide acrylates, tetraethylene glycol diacrylate, and zinc acrylate, which are commercially available (e.g., from Sigma Aldrich, Polysciences, etc.) or described in the art (e.g., see U.S. Pat. No. 5,474,915).

Other exemplary hydrogel-forming materials containing polymerizable groups are polymerizable polymers such as trimethylolpropane ethoxylate triacrylate, multi-arm polyethylene glycol (PEG) acrylates, multi-arm PEG dimethacrylates, PEG diacrylates, PEG dimethacrylates, polypropylene glycol (PPG) diacrylates, PPG dimethacrylates, which are commercially available (e.g., from Sigma Aldrich, Polysciences, etc.) or described in the art (e.g., see U.S. Pat. No. 4,424,311). Polymerizable polymers can also be formed using hydrophilic polymers such as poly(vinylpyrrolidone) (PVP), poly(ethylene oxide) (PEO), poly(ethyloxazoline), poly(propylene oxide) (PPO), poly(meth)acrylamide (PAA) and poly(meth)acrylic acid, poly(ethylene glycol) (PEG), PEG-PPO (copolymers of polyethylene glycol and polypropylene oxide), hydrophilic segmented urethanes, and polyvinyl alcohol.

An adhesive with silk fibroin and a hydrogel forming material can also include a chemical initiator, such as a photoinitiator, which can be treated with radiation to initiate crosslink of the hydrogel-forming materials. Examples of initiators include 4-hydroxybenzophenone, 2-hydroxy-4'-(2-hydroxyethoxy)-2-methylpropiophenone, 2,2-dimethoxy-2-phenylacetophenone, 4-aminobenzophenone, acetophenone, 2,2-diethoxyacetophenone and more.

Silk fibroin-containing adhesive compositions are described in commonly-assigned U.S. Patent Application Ser. No. 61/745,361 (Dec. 21, 2012).

FIG. 3b shows an embodiment of a leaf 10a or 10b with elongate patches 112a extending continuously (alternately with interruptions) along a length of leaf 10a or 10b. According to this embodiment, leaf 10a or 10b can be folded between patches 112 to reduce the profile of leaf 10a or 10b for surgical insertion (e.g., laparoscopically) into a patient.

In use, implant 10 may be introduced to a patient pelvic region and placed at vaginal tissue laparoscopically in a sacral colpopexy procedure by steps, optionally including the use of a dilator as described herein, as follows. A surgeon may manipulate a dilator as described herein to control or support vaginal tissue near a vaginal cuff, during laparoscopic placement of implant 10 into the patient, during laparoscopic placement of vaginal leafs 10a, 10b of implant 10 at vaginal tissue anterior and posterior to the vaginal cuff, and during laparoscopic placement of vaginal leafs 10a and 10b in contact with anterior and posterior tissue of a vaginal cuff in a manner that places adhesive 112 in contact with outer vaginal tissue 23. Implant 10 may be reduced in size or profile by folding, e.g., along a length, to allow laparoscopically passing the folded implant 10 into the patient. Dilator 20 may remain in the vagina of the patient for a time during or after the surgery to allow the adhesive 112 to become secured to outer vaginal tissue 23, to allow tissue ingrowth at the implant, to allow leafs 10a, 10b to be secured to vaginal tissue by use of a different type of fastener, or a combination of two or more of these.

A deployment tool 30 is illustrated in FIGS. 4*a-d,* which is adapted to be useful to allow insertion of a Y-sling 10 through a laparoscopic incision and placement of the Y-sling at posterior vaginal tissue. Deployment tool 30 has a handle 32, shaft 36, and sheath 34 having open end 34*a;* shaft 36 and sheath 34 can preferably fit within and through a hollow laparoscopic trocar or laparoscopic port to allow sheath 34 to be passed laparoscopically into a pelvic region of a patient for laparoscopic delivery of a Y-sling 10 for attachment to vaginal tissue. During insertion of implant 10 laparoscopically into a patient pelvic region, through a laparoscopic incision, the deployment tool 30 holds the Y-sling 10 within the sheath 34 (see FIG. 4*d*); the Y-sling 10 is in a compressed or folded state within sheath 34 (see FIGS. 4*a* and 4*b*). To pass Y-sling 10 through and out of open end 34*a* and into the patient pelvic region at or near vaginal tissue, when deployment is desired, sheath 34 can be retracted relative to shaft 35 to push Y-sling 10 through open end 34*a* for placement at target tissue in a sacral colpopexy.

Optionally, the Y-sling 10 may have a shape memory frame (see, e.g., FIGS. 4*c,* 5*a,* 5*b,* 13*a,* 13*b,* 14*a,* 14*b,* and related text) adapted to cause Y-sling 10 to open or otherwise take on a supported form adapted for placement of Y-sling 10 or a component thereof (e.g., leaf 10*a,* 10*b*) in a manner that conforms to outer vaginal tissue 23, e.g., once deployed from the sheath 34. The Y-sling 10 unfolds, expands, or is supported by frame 130 in a deployed state once sheath 34 is removed. The frame 130 includes one or more structural features that can allow implant 10 to be folded or collapsed to a shape and size that allow the folded implant to be placed within a sheath 34 of tool 30. Upon deploying implant 10 from sheath 34 at a surgical site within a patient, the frame supports Y-sling 10, optionally also causing Y-sling 10 to expand or unfold. Frame 130 may be linear, cornered, curved, or a combination thereof, in a manner to give shape or support to an implant (i.e., a "stiffener," "strut," or "support," etc.). A frame 130 can be located at a surface or edge of an implant to cause the implant to spread out to a desired shape upon placement within a patient. As used herein, the term "spread" refers to an implant or implant portion that is in a deployed, open, e.g., unfolded, configuration; likewise, the term "unspread" refers to an implant that is either to some degree folded or rolled onto itself (see FIG. 4*a*), particularly to a configuration capable of passing through a laparoscopic trocar and laparoscopic incision.

A frame provides added shape-retention to facilitate placement of an implant at a desired position within a patient, so the implant can take on a spread configuration to achieve full size and to cover a fully-expanded area without unwanted folding. The frame may be linear, flat, curved, or otherwise shaped in a manner that adapts the implant to patient anatomy, e.g., shaped to match a shape of an outer surface of vaginal tissue anterior and posterior to a vaginal vault, supported by a method of sacral colpopexy.

A frame may be a discrete element of an implant that is more rigid than the implant material (e.g., mesh, biologic material, extruded or molded polymer), and may be shaped and incorporated into the structure of the implant to improve the ability of the implant to take on and maintain a desired flat or shaped configuration upon being placed laparoscopically within a pelvic region of a patient. A frame 130 may be a plastic material such as a plastic strip that is attached to an implant along an edge or along a length of a surface of an implant. Alternate frames may be shape memory metal (e.g., nitinol) that may be compressed to allow implant 10 to be folded or compressed for placement within sheath 34, and biased to expand upon being deployed from sheath 34. The frame may be flexible to some degree yet still provide a degree of rigidity and support to prevent the implant from becoming undesirably folded by preventing folding of the implant in a direction that would fold or bend the frame. The frame can be straight, curved, or cornered, and optionally biased, e.g., in a spring-like fashion. The frame can be placed along a single edge of an implant, along opposing edges, or one or more frames can be placed along multiple edges of an implant or a portion of an implant extending around a perimeter or a portion of a perimeter of an implant or a portion of an implant, or along a length of a portion of an implant such as longitudinally along a length of a vaginal leaf 10*a,* 10*b.* As yet another alternative, one or more frames can be used to shape and support (e.g., stiffen) a surface area of an implant or a portion of an implant by being placed at a surface of the implant away from edges, e.g., along a length of a vaginal leaf 10*a,* 10*b.*

Figure 5A:
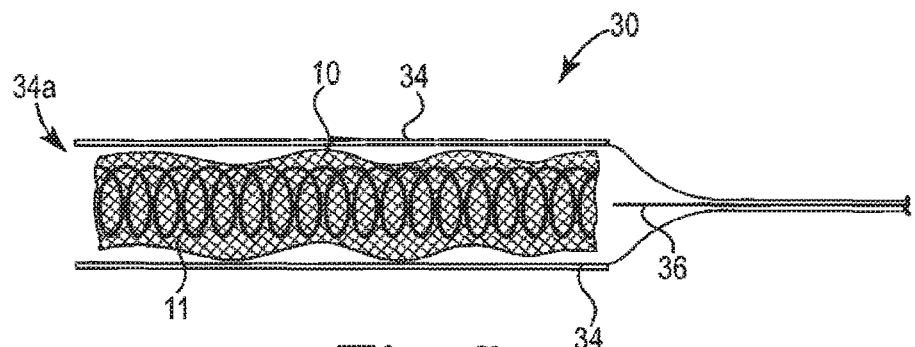
FIGS. 5a and 5b illustrate a cross sectional view of a deployment tool.
Figure 5B:
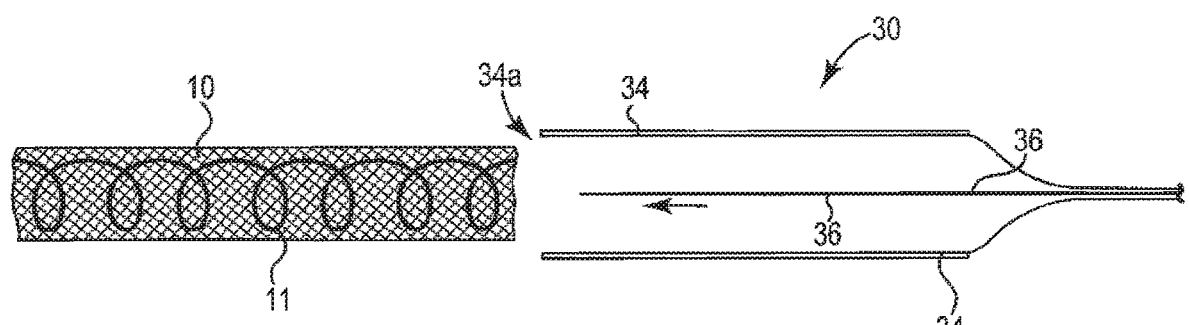

FIGS. 5*a* and 5*b* illustrate an alternative deployment tool 30 containing implant 10 with frames 11 in the form of a biased metal or plastic expandable frame 11. Deployment tool 30 may have a handle 32 on the proximal end, a hollow sheath 34 having an open distal end 34*a,* and longitudinally-moveable inner shaft 36. A Y-sling 10 may be placed within hollow sheath 34 at a distal end of tool 30, which can be placed, e.g., laparoscopically, at a surgical site for a sacral colpopexy. Y-sling 10 may have a nitinol expansion spring coil frame 11 that is compressed while contained by sheath 34, and that releases upon deployment from sheath 34; Y-sling 10 may be held in place by the sheath 34 until deployment by longitudinal (distal) movement of shaft 36 to push Y-sling 10 from the open end 34*a* of sheath 34. Before deployment, Y-sling 10 is contained within hollow sheath 34 (see FIG. 5*a*). During deployment, Y-sling 10 may be incrementally extended out through open distal end 34*a* by longitudinal movement of shaft 36 in a distal direction (see arrow at FIG. 5*b*). A physician can fasten Y-sling 10 to vaginal tissue or tissue of a region of sacral anatomy as Y-sling 10 is deployed incrementally.

Figure 13A:
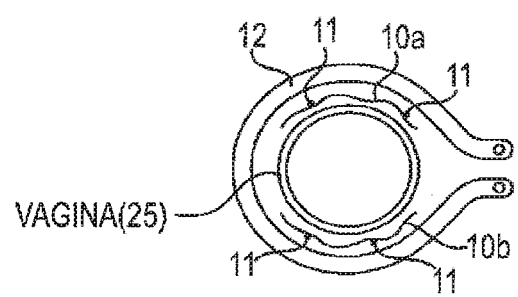
FIGS. 13a and 13b show end and side perspective views of a Y-sling with a frame or wire support.
Figure 13B:
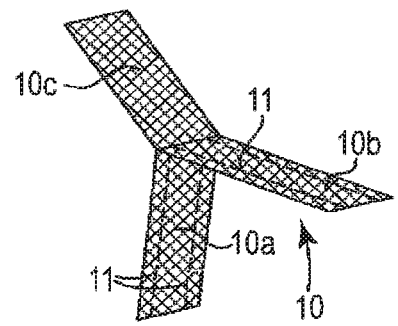

In another embodiment, Y-sling 10 may also have a support wire (frame) 11 as shown at FIGS. 13*a* and 13*b.* The support wire (frame) 11 extends longitudinally along lengths of each of vaginal leafs 10*a* and 10*b,* which may be flat or curved, e.g., shaped to adapt to a surface of outer vaginal tissue at or adjacent to a vaginal cuff. During placement, frame 11 may cause each leaf 10*a,* 10*b* to maintain a desired shaped or flat form along a length of the vaginal tissue. FIG. 13*a* illustrates a cross-sectional view of the Y-sling 10 with support wire (frame) 11 around the vagina.

Figure 14A:
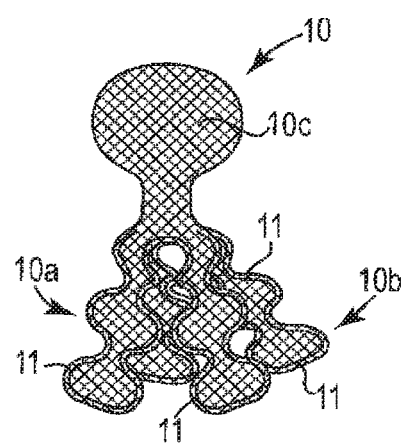
FIGS. 14a and 14b show side and end views of a Y-sling with a frame or wire support.
Figure 14B:
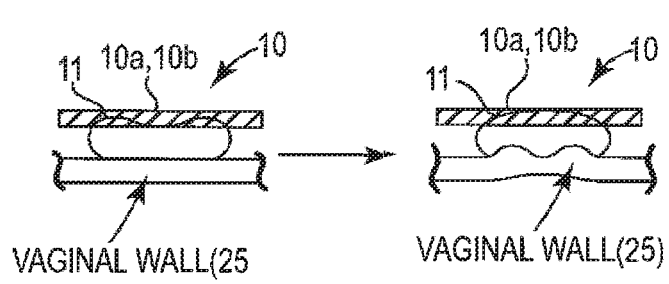

FIGS. 14*a* and 14*b* illustrate another embodiment of a Y-sling 10 having support wire or frame 11. As illustrated, each of leafs 10*a* and 10*b* includes a frame (e.g., wire) 11 that causes the leaf to assume multiple rounded, regular or irregular shaped forms extending along a length of each leaf. Frame 11 may be biased (e.g., by molding) so that upon placement on the vaginal tissue 25, frame 11 pinches the tissue (see FIG. 14*b,* right). The pinching of tissue can maintain the placement of Y-sling 10 at one or more sites for placing a fastener at the leaf to fasten leaf 10*a* or 10*b* to vaginal tissue 25.

Figure 6:
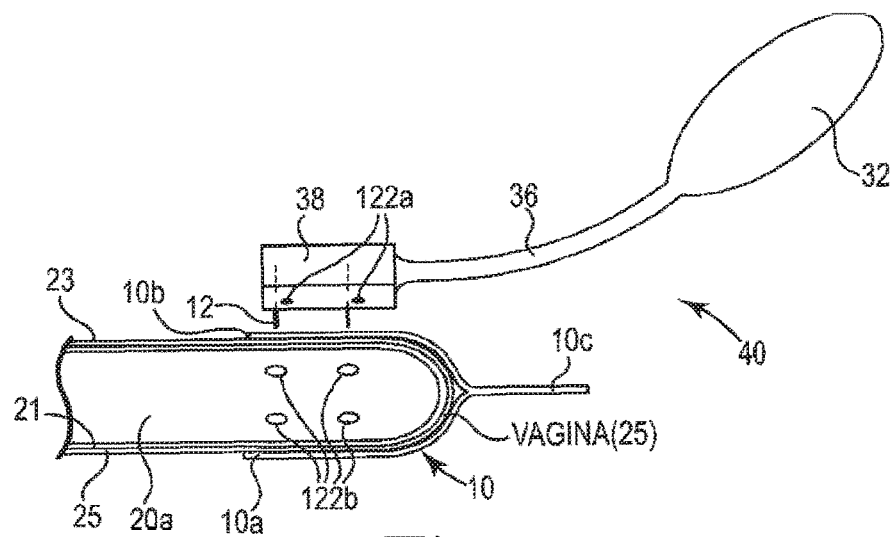
FIG. 6 shows a side view of a dilator, Y-sling, and securement tool.

FIG. 6 illustrates an embodiment of an attachment tool 40. Attachment tool 40 has a handle 32, shaft 36, and a means for attachment 38, which includes a mechanical fastener dispenser capable of placing a fastener 12 at a vaginal leaf 10*a,* 10*b,* to secure leaf 10*a,* 10*b* to vaginal tissue 25 at outer vaginal tissue 23; preferably the fastener 12 does not penetrate vaginal tissue 25 or puncture, cut, sever, or otherwise disrupt a surface of inner vaginal tissue 21. The attachment tool 40 is inserted, e.g., laparoscopically, through the peritoneal cavity to the fastening point of the Y-sling 10 (vaginal leaf 10a, 10b) to anterior or posterior tissue of the vaginal cuff. The means for attachment 38 can house one or multiple fasteners 12 at a distal end of tool 40, and can be adapted to dispense fastener 12 to secure implant 10 to vaginal tissue 25. A fastener 12 may be one or more suture, staple, clip, barb, tine, hook, or other like mechanical fastener. As illustrated, dilator 20a and attachment tool 40 may both have one or a series of opposite-pole magnets 122a and 112b that allow means for attachment 38 to magnetically align correctly with a complementary alignment mechanism (opposed magnets) 122b located at a distal end of dilator 20a.

In use, implant 10 (e.g., including any optional feature as described herein) may be placed laparoscopically in a sacral colpopexy procedure by steps, including the use of a dilator 20a, as follows. A surgeon may manipulate dilator 20a as described herein to control or support vaginal tissue near a vaginal cuff, during laparoscopic placement of implant 10 into the patient, during laparoscopic placement of vaginal leafs of implant 10 at vaginal tissue anterior and posterior to the vaginal cuff, and during laparoscopic placement of one or multiple fasteners 12. Accordingly, magnets 122a located at a distal end of tool 40 adjacent to means for attachment 38 can be placed in magnetic communication with and alignment with magnets 122b of dilator 20a, to properly and predictably locate and place fasteners 12 at desired locations for securing vaginal leafs 10a, 10b to vaginal tissue 25, preferably without puncturing, cutting, severing, or otherwise disrupting a surface of inner vaginal tissue 21. Tool 40 may be inserted laparoscopically or through an abdominal incision. Upon alignment between magnets 122a and 122b, fasteners 12 can be dispensed to secure implant 10 (e.g., vaginal leaf 10a, 10b) to vaginal tissue 25.

Figure 7A:
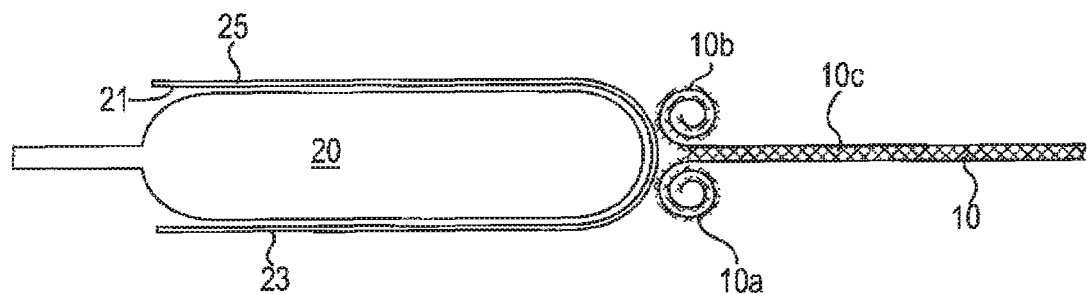
FIGS. 7a and 7b show side views of a dilator and Y-sling.
Figure 7B:
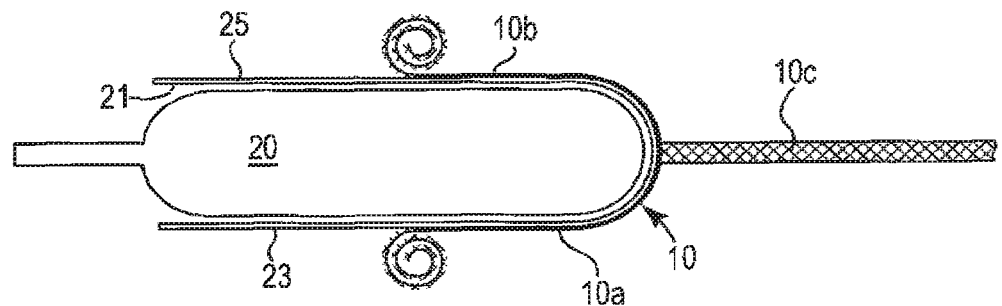

FIGS. 7a (side view) and 7b (side view) show an embodiment of a Y-sling 10 and dilator 20. Dilator 20 supports tissue of vagina 25 during placement of Y-sling 10 in a sacral colpopexy procedure. Y-sling 10 can be introduced (e.g., laparoscopically) at a region of outside vaginal tissue 23. Y-sling 10 includes vaginal leafs 10a, 10b, which in a non-deployed configuration are rolled up as shown at FIG. 7a; in this rolled-up configuration each leaf has been rolled starting at a distal end (at the inside of each roll), in a direction toward sacral leaf 10c, to produce two rolls or coils of each leaf 10a, 10b. With leafs 10a, 10b in the rolled, non-deployed configuration (FIG. 7a), implant 10 may be passed into a patient, e.g., laparoscopically through a laparoscopic trocar (having a diameter of not greater than 1 centimeter, e.g., not greater than 8 millimeters or not greater than 6 millimeters), or alternately through an abdominal incision. Once located at a region of the vaginal cuff, each rolled leaf 10a, 10b may be un-rolled in a manner that causes a surface of each leaf 10a, 10b to become located at outside tissue 23 at a posterior and an anterior of vagina 25; an anterior vaginal leaf becomes positioned at anterior vaginal tissue on an anterior (or superior) location of vagina 25, and a posterior vaginal leaf becomes positioned at posterior vaginal tissue on a posterior (or inferior) location of vagina 25, as occurs with placement of a Y-mesh in a typical sacral colpopexy. This Y-sling 10 can be sized accordingly to reduce bulk in the patient. A physician can fasten Y-sling 10 to the vaginal tissue as Y-sling 10 is being un-rolled down and around the vagina. Optionally, each leaf 10a, 10b, in a rolled configuration (see FIG. 7a) or a un-rolled configuration (see FIG. 7b) may be coated with a stiffening agent such as starch, mannitol, dextrose, sorbose, sucrose, a salts, e.g., sodium chloride, potassium chloride, sodium carbonate, polyvinylpyrrolidone (PVP), or any other biocompatible agent that may be useful to bias the shape of a leaf 10a, 10b, in the rolled or un-rolled configuration, as desired, while allowing or facilitating the rolled leaf 10a, 10b, to be un-rolled as desired onto vaginal tissue as described.

In use, implant 10 may be introduced to a patient pelvic region and placed at vaginal tissue laparoscopically in a sacral colpopexy procedure by steps, optionally including the use of a dilator as described herein, as follows. A surgeon may manipulate a dilator as described herein to control or support vaginal tissue near a vaginal cuff, during laparoscopic placement of implant 10 into the patient, during laparoscopic placement of vaginal leafs 10a, 10b of implant 10 at vaginal tissue anterior and posterior to the vaginal cuff, and during laparoscopic placement of vaginal leafs 10a and 10b in contact with anterior and posterior tissue of a vaginal cuff. During placement of leafs 10a, 10b, each leaf may be secured to vaginal tissue 25 by any manner, such as any one of the specific modes of attachment described herein, preferably without passing any type of mechanical fastener structure through an entire thickness of vaginal tissue 25, i.e., without puncturing, cutting, severing, or otherwise disrupting a surface of inner vaginal tissue 21.

Figure 8A:
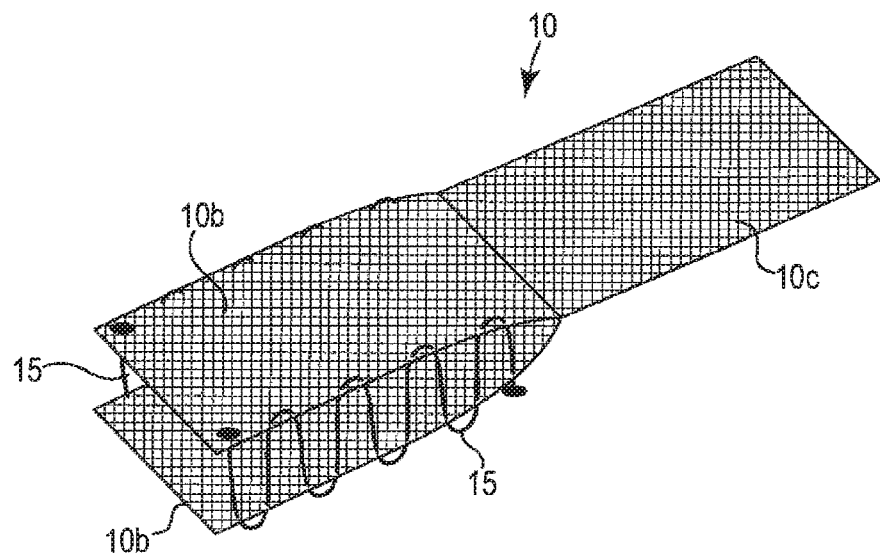
FIGS. 8a and 8b show side perspective views of a Y-sling and optional dilator.
Figure 8B:
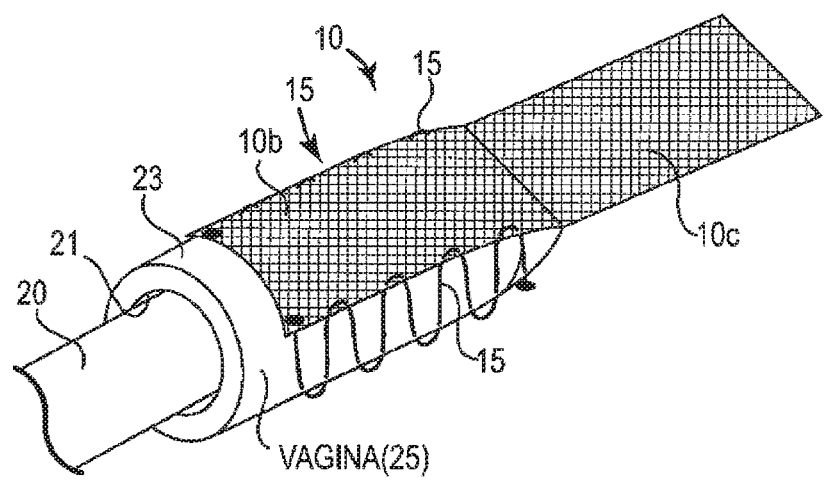

FIGS. 8a and 8b illustrate an alternative embodiment of a Y-sling 10 wherein vaginal leafs 10a, 10b are connected along opposing longitudinal edges in a manner that allows tightening of the leafs together after placement of the leafs at vaginal tissue during sacral colpopexy (see FIG. 8b). As illustrated, connector 15 is a filamentary connector such as a natural or polymeric suture, thread, or elastomeric band material. Upon placement of leafs 10a, 10b as illustrated at FIG. 8b, connector 15 may be manipulated to cause opposing edges of leafs 10a, 10b to be pulled toward vaginal tissue and the opposed edge, thereby creating a cylindrical form of the leafs 10a, 10, about vaginal tissue 25 (with lateral edges remaining open other than the presence of connectors 15). In use, with optional dilator 20 placed within vagina 25, Y-sling 10 is introduced to a surgical site and region of vagina 25, e.g., laparoscopically or through an abdominal incision. Opposed leafs 10a, 10b, are placed over the vaginal cuff as shown at FIG. 8b, in contact with tissue anterior to and posterior to the vaginal cuff. Connector 15 can be pulled provide tension in connector 15 causing edges of leafs 10a, 10b, to be pulled and move toward each other, placing tension on each leaf 10a, 10b in contact with outer vaginal tissue 23 and increasing a frictional hold between each inner surface of leaf 10a and 10b, and outer vaginal tissue 23, to inhibit movement between leafs 10a, 10b, and the outer vaginal tissue 23, e.g., to cause Y-sling 10 to be held in place during a subsequent fastening with an alternate fastener (e.g., suture, staple, adhesive, etc.). With connectors 15 tightened, each leaf 10a, 10b, may be secured to vaginal tissue 25 in any manner, such as any one of the specific modes of attachment described herein, preferably without passing any portion of a mechanical fastener through an entire thickness of vaginal tissue 25, i.e., without puncturing, cutting, severing, or otherwise disrupting a surface of inner vaginal tissue 21. After implant 10 is placed for sacral colpopexy, including leafs 10a, 10b being fastened as desired to the tissue anterior to and posterior to the vaginal cuff, the connectors 15 can be cut and removed from the body, e.g., laparoscopically; alternately connectors 15 may be bioabsorbable or permanent.

Additionally or alternatively, a Y-sling 10 may be coated with a coating such that the coating acts as a fastener in the form of a temporary or permanent adhesive or sticky substance (see FIGS. 3a and 3b). For example a bioadhesive or sticky coating substance may be used to hold leafs 10a, 10b, in place during a sacral colpopexy procedure for a time sufficient to allow another fastener (e.g., suture, staple, etc.) to be placed to more permanently secure leaf 10a or 10b to the vaginal tissue. The coating could be a hydrometric acid, cyanoacrylate or other hydrogel, albumen, antibacterial agent or other similar surface treatment, or an adhesive such as described herein (see FIG. 3 and related text). An exemplary embodiment of a coating would be one that is non-adherent when present on a non-deployed Y-sling, and then becomes adherent to vaginal tissue upon being placed in contact with vaginal tissue and hydrated.

Figure 9:
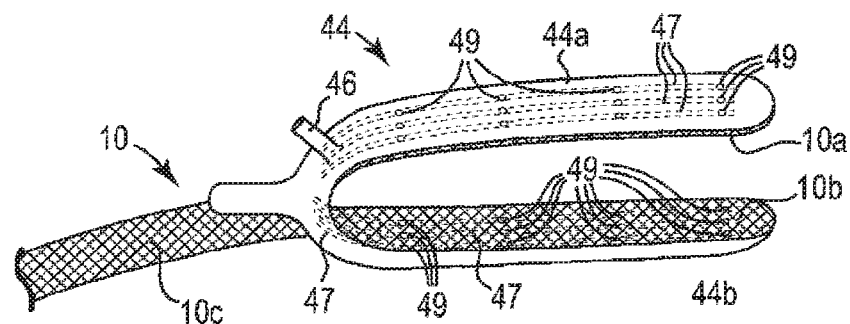
FIG. 9 shows a Y-mesh and applicator.

Alternately, a coating or adhesive as described may be applied by an applicator as shown at FIG. 9. The coating may be a bioadhesive that permanently or temporarily secures leafs 10a, 10b, to vaginal tissue. Applicator 44, may be placed around an exterior surface of Y-sling 10 as shown in FIG. 9, during a sacral colpopexy procedure, after Y-sling 10 is positioned about a vaginal cuff. Applicator 44 includes anterior portion 44a and posterior portion 44b, positionable at tissue anterior to a vaginal cuff and posterior to a vaginal cuff, respectively. Injection port 46 is in fluid communication with dispensing channels 47 of anterior and posterior portions 44a, 44b. Dispensing channels 47 lead to openings 49 at surfaces of anterior and posterior portions 44a, 44b; the openings open to a location of leafs 10a, 10b, and vaginal tissue, when applicator 44 is placed at a surgical dispensing position about vaginal tissue 25 with leafs 10a, 10b previously positioned on vaginal tissue 25.

During use, leafs 10a, 10b and implant 10 are placed, e.g., laparoscopically, at anterior and posterior tissues of the vaginal cuff during a sacral colpopexy procedure. Applicator 44 is placed (e.g., laparoscopically) over the leafs 10a, 10b, and over vaginal tissue 25 (not shown), placing openings 49 at a surface of leafs 10a, 10b, which leafs are adjacent to vaginal tissue 25. A coating or adhesive can be dispensed with moderate pressure through port 46 and caused to flow through channels 47 and exit openings 49 of anterior and posterior portions 44a, 44b. The coating or adhesive flows from openings 49 to contact leafs 10a, 10b and adjacent tissue of vagina 25, securing leafs 10a, 10b, to vaginal tissue at anterior and posterior portions of the vaginal cuff. After a coating or adhesive is dispensed, applicator 44 can be removed. The procedure may be a sacral colpopexy performed by way of an abdominal incision or laparoscopically. Also optionally, the sacral colpopexy may be performed in combination with a dilator placed within vagina 25 to support vaginal tissue 25 during the procedure, the dilator being any dilator, such as a dilator 20 described herein.

Figure 10A:
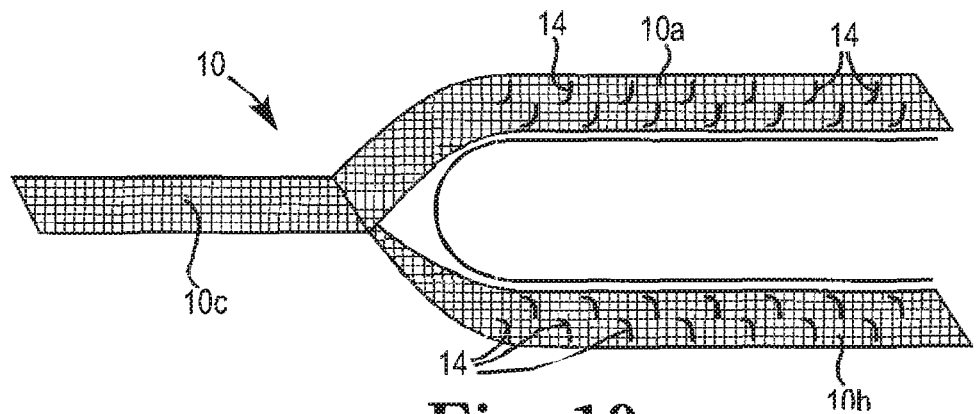
FIGS. 10a and 10b show side perspective views of a Y-sling with fasteners.
Figure 10B:
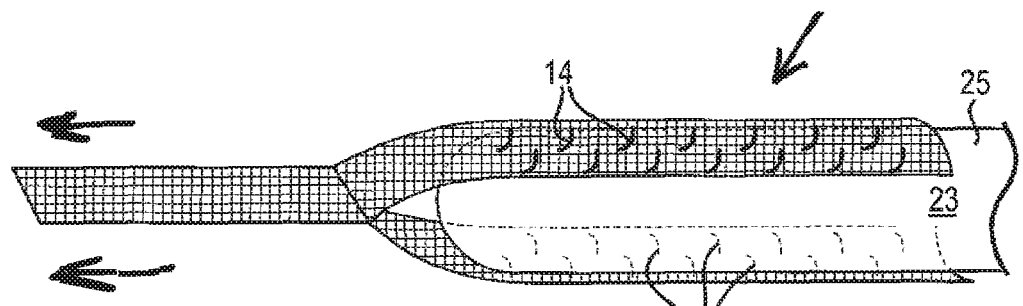

FIGS. 10a, 10b, 10c, 10d, and 10e show alternate methods and implants 10 wherein a Y-sling 10 includes fasteners pre-placed (e.g., injection molded) and located on a surface of leafs 10a, 10b, the fasteners being adapted to penetrate into vaginal tissue 25, optionally and preferably without penetrating through the full thickness of vaginal tissue 25. The fasteners penetrate the vaginal tissue in a manner and to an extent to secure leafs 10a, 10b to anterior or posterior tissue of a vaginal cuff for sacral colpopexy, either permanently or temporarily for a time sufficient to place additional fasteners (e.g., sutures or staples) to more permanently secure the leaf 10a, 10b to the vaginal tissue. Preferred such fasteners (e.g., 14 as shown at FIGS. 10a and 10b) can contact and penetrate into vaginal tissue 25 through a surface at outside vaginal tissue 23 by use of light pressure placed on the fastener in a direction to push or pull the fasteners 14 into the tissue during a sacral colpopexy procedure (see arrows at FIGS. 10b, 10c, 10d, and 10e). For example, Y-sling 10 may include on inner surfaces of leafs 10a, 10b (i.e., the surfaces facing toward the surface of outside vaginal tissue 23) (see FIG. 10b), barbs, tines, barbed tines, tangs, straight or bent extensions, or hooks 14 that may be sufficiently sharp and shaped to be pressed or pulled into vaginal tissue 25; optionally but not necessarily, a fastener 14 may also include structure such as a barb that, after placement of fastener 14 within tissue 25, resists movement of fastener 14 in a direction that would allow fastener 14 to become removed from tissue 25. The fasteners may be made of metal or plastic, e.g., molded or injection molder polymer, to provide a fastener having an elongate shaft, a sharpened end, and one or more optional frictional features along the shaft such as a tine, barb, ridge, or the like, adapted to allow the sharp extension to be pressed or pulled into but not entirely through vaginal a complete thickness of tissue with the optional frictional feature resisting removal of the fastener 14 from the vaginal tissue (see FIG. 10d).

Any of the described or illustrated types of fasteners 14 may be made by various methods. Fasteners may be made separately, e.g., by injection molding or heat forming, etc., and then secured to an implant material for use at an inner surface of a leaf 10a, 10b. In alternate methods, a leaf 10a, 10b or a component thereof (e.g., a strand of a woven or knit leaf, or a polymer film) can be molded (e.g., injection molded) to include a fastener at a surface. A fastener may be made of a material that is the same as the leaf 10a, 10b, or different.

Figure 10C:
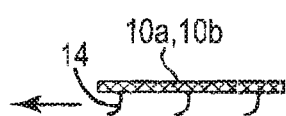
FIGS. 10c, 10d, and 10e are detail views of these and alternate fasteners.
Figure 10D:
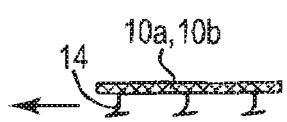
Figure 10E:
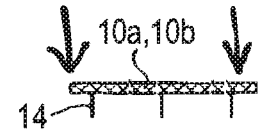

FIG. 10d shows an embodiment of fastener 14 that includes an elongate shaft and a barb at a distal end of the shaft; in use the barb can penetrate into vaginal tissue and prevent removal of fastener 14 from the tissue; the fastener 14 may be curved, straight, or slanted such that when leaf 10a, 10b is pulled away from vaginal tissue (see arrow at FIGS. 10b and 10c) while fasteners 14 are in contact with a surface of the vaginal tissue, curved (alternately straight slanted toward sacral leaf 10c) fasteners 14 are caused to advance into the vaginal tissue and penetrate the tissue. FIG. 10c shows a curved "hook"-type fastener 14 that includes a curved shaft but no barb. FIG. 10e shows fastener 14 that includes a straight shaft and no barb (alternate straight shafts may be slanted or may include a barb at a distal end).

The fasteners (e.g., barbs or hooks) 14 can be pressed or pulled into and embedded in vaginal tissue with a light pressure applied to leaf 10a, 10b in the form of a pulling force (see FIGS. 10c and 10d) or a pressing force directed toward a tissue surface (see FIG. 10e). The force may be applied by use of a surgical instrument, e.g., laparoscopically. The fasteners (e.g., shafts, extensions, barbs or hooks) 14 may be made from a metal, polymeric plastic, optionally bioresorbable material, biocompatible material, or any combination thereof, formed on or placed upon the opposed inner surfaces of leafs 10a, 10b. Fasteners (e.g., barbs or hooks) 14 are preferably of a height dimension (e.g., height from the inner surfaces of leafs 10a, 10b) that is substantially less than a thickness of a vaginal tissue (meaning the distance between an inner vaginal surface and an outer vaginal surface); this allows a fastener 14 to penetrate into less than the full thickness of vaginal tissue 25, i.e., to prevent the fastener from passing through the tissue to puncture, cut, sever, or otherwise disrupt a surface of inner vaginal tissue 21.

In use with an optional dilator 20 placed within vagina 25, Y-sling 10 is introduced to a surgical site at a region of vagina 25, e.g., laparoscopically or through an abdominal incision. Opposed leafs 10a, 10b, having fasteners 14 on opposed inner surfaces thereof (see FIG. 10a) are placed over the vaginal cuff at a surface of outside vaginal tissue 23 as shown at FIG. 10b. Leafs 10a, 10b are placed to contact posterior and anterior vaginal tissue at the vaginal cuff. Fasteners 14 on inner surface of leafs 10a, 10b, contact the anterior and posterior tissues of the vaginal cuff. Pressure can be applied on the opposite (outer) surfaces of leafs 10a and 10b, or by pulling implant 10 (see FIGS. 10c and 10d) to cause fasteners 14 to penetrate vaginal tissue 25 and cause leafs 10a and 10b to become at least temporarily secure against outer vaginal tissue 23. Optionally, one or more additional fastener can be placed at leafs 10a, 10b to permanently secure leafs 10a, 10b to vaginal tissue 25.

In yet another alternate embodiment, a sacral colpopexy may be performed using a system that includes an implant 10, an optional dilator, and a clip 19 that includes fasteners 16 on a surface (an inner surface), the fasteners being adapted to pass through a thickness of a mesh implant (e.g., leafs 10a, 10b) and into a surface of outer vaginal tissue, preferably without penetrating through a full thickness of the vaginal tissue. Fasteners 16 can pass through leafs 10a, 10b, and into vaginal tissue 25 to hold leafs 10a, 10b (e.g., temporarily) against vaginal tissue 25, then be removed without causing undue trauma to vaginal tissue 25.

Figure 11A:
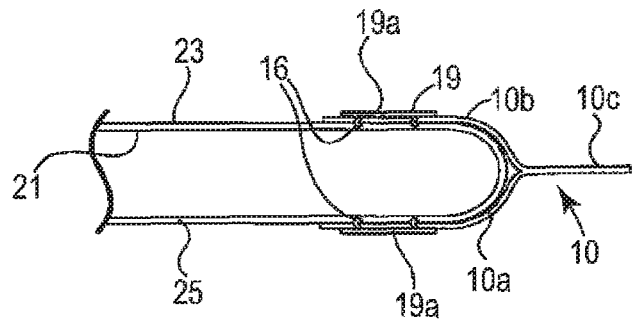
FIGS. 11a, 11b, and 11c show side and end-views of a clip and optional dilator.
Figure 11B:
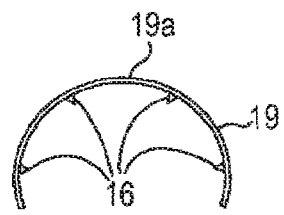
Figure 11C:
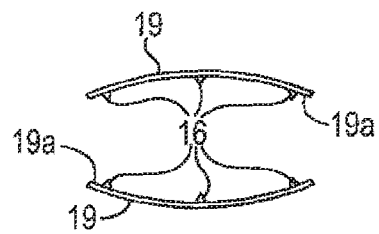

An exemplary clip 19 can include a backer 19a, e.g., in the form of a flat or curved surface that can be placed against vaginal tissue 25; the surface may be flat or curved to fit a form of vaginal tissue, e.g., at an anterior or posterior location of a curved vaginal cuff. Backer 19a may include an upper (anterior) portion and a lower (posterior) portion, one each for contacting tissue of an anterior and posterior vaginal cuff; the upper and lower portions may be separate or connected to each other. One example is a clip having a rounded or curved cross-section that fits about a portion of an outer surface of vaginal tissue, including a length that extends along a length of the vaginal tissue near and anterior to or posterior to the vaginal cuff. The length of clip 19 may be approximately the same as or somewhat less than a length of a vaginal leaf 10a or 10b of an implant 10 (see FIG. 11a), at a location of contact between the leaf 10a or 10b and outer vaginal tissue 23.

Clip 19 may be useful to temporarily maintain placement of Y-sling 10 against vaginal tissue 25 during a sacral colpopexy procedure. Clip 19 may be removable (e.g., laparoscopically) from the Y-sling 10 and vaginal tissue after placement of the Y-sling 10 and after the Y-sling 10 has been secured to vaginal tissue 25 by tissue ingrowth or by placement of one or more alternate fastening mechanism (other than clip 19) such as one described herein. Fastener 16 may be any fastener, including any of the fasteners generally or specifically described herein, e.g., with respect to FIGS. 10a through 10e, and are preferably of dimensions (e.g., height from the inner surfaces of leafs 10a, 10b) to allow a fastener 16 to pass through material of a leaf 10a or 10b to contact and frictionally engage an outer surface 23 of vaginal tissue 25 with sufficient frictional force to retain leafs 10a and 10b in place during a sacral colpopexy. Optionally and preferably, fasteners 16 are adapted to pass through a leaf 10a or 10b and pass through the surface of outer vaginal tissue 23 and to penetrate a portion of a thickness of vaginal tissue 25, preferably without passing through the full thickness of the vaginal tissue and without puncturing, cutting, severing, or otherwise disrupting a surface of inner vaginal tissue 21. In one embodiment, fastener 16 may be a sharp or non-sharp elongate un-barbed elongate tine, elongate shaft, or other un-barbed extension that can penetrate into vaginal tissue 25 without passing through the full thickness of the vaginal tissue 25, and may thereafter be removed from vaginal tissue 25 without causing undue trauma or disrupting the tissue.

Figure 12:
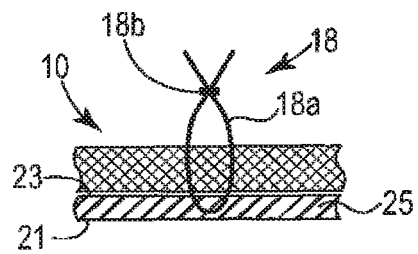
FIG. 12 shows a knotless suturing method and structure.

FIG. 12 illustrates a device and method for connecting a suture 18 to itself without the use of knotting. Such a knotless suture may be useful to attach a portion of an implant to tissue, for example as described herein, to attach a portion of a Y-sling to vaginal tissue or to tissue at a region of sacral anatomy. Suture 18 is a polymeric material that may be caused to melt to bond one portion of the suture to another portion, after an intermediate loop of the suture 18 has been passed through material of the Y-sling and through vaginal tissue 25. One portion of the suture may be capable of being bonded to another portion of the same suture itself, by any one of heating (heat or thermal bonding), ultrasonic welding, or the like. In an exemplary embodiment a loop 18a is formed through implant 10 and tissue 25, after which energy (e.g., ultrasonic energy) is applied to suture 18 where a knot is otherwise desired, such as at connection 18b. The energy (e.g., ultrasonic energy) applied to the two contacting portions of suture 18 at connection 18b causes the two portions to melt and become bonded together, making connection 18b without the need to form a knot in the suture 18. Other techniques for melting suture such as using heat energy or pressure sensitive materials may alternately be useful. These method steps can be useful with any form of implant or implantation method, including any of the forms of Y-slings described herein, with any features; the method steps can be preformed in conjunction with any other method steps described herein, such as with the use of any of the different dilators described herein to support vaginal tissue during a step of attaching an implant material to the vaginal tissue, using a suture 18.

Figure 15A:
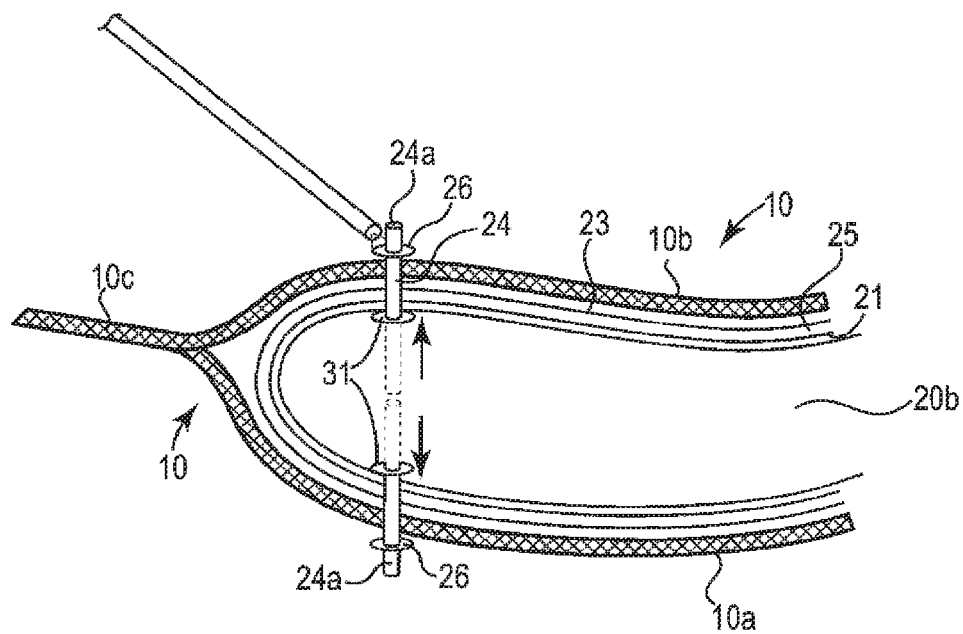
FIGS. 15a and 15b illustrate embodiments of a dilator and Y-sling.

FIG. 15a shows an example of another dilator 20b useful in any one of the systems or methods described, and with any of the various Y-mesh designs an Y-mesh features. Dilator 20b includes mechanical extensions 24 that can be extended and retracted from apertures 31 at a distal end of a surface of dilator 20b, while dilator 20b is installed in a patient for use in a sacral colpopexy, at a location near a vaginal cuff. One or more extensions 24 can be extended to contact and pass through vaginal tissue 25 and extend through leafs 10a and 10b located at posterior and anterior tissue of a vaginal cuff (see FIG. 15a). An external portion 24a of an extension 24 passes through the vaginal tissue and extends to a location exterior to the vagina, e.g., at the peritoneal cavity, to also pass through a full thickness of vaginal leaf 10a or 10b. When so located, a grommet 26 may be placed over the end of the external portion 24a to maintain the position of leaf 10a or 10b against vaginal tissue 25. The external portion 24a and grommet 26 function to hold leaf 10a or 10b of Y-sling 10 in place while a more permanent attachment means or fastener is placed to secure leaf 10a or 10b at the surface of outer vaginal tissue 23. Once the Y-sling 10 is attached to the vaginal apex, grommet 26, external posts 24, and dilator 20b can be removed. The steps of attaching and detaching grommet 26 to external portion 24a may be performed laparoscopically or through an abdominal incision.

Figure 15B:
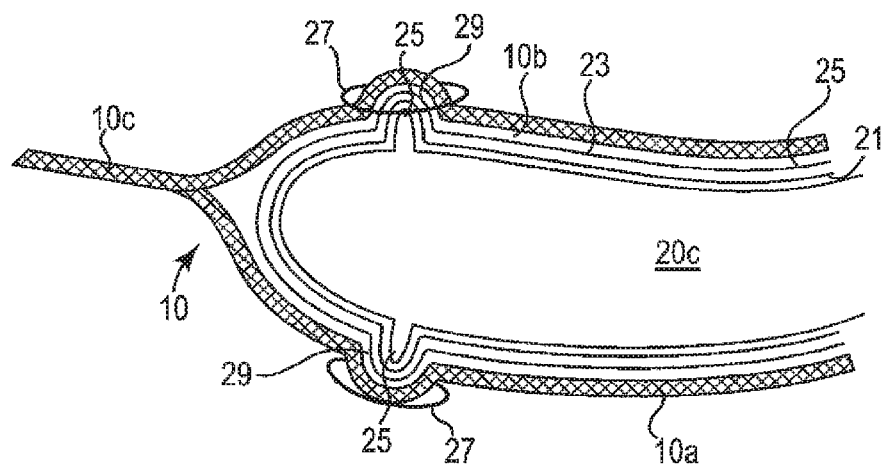

FIG. 15b shows an alternate example of another dilator, 20c, useful in any one of the systems or methods described herein, and with any of the various featured Y-slings. Dilator 20c includes protrusions or extensions 25 that can optionally be extended and retracted at a distal end of a surface of dilator 20c, while dilator 20c is installed in a patient for use in a sacral colpopexy and at a location near a vaginal cuff.

One or more extensions 25 can be extended to contact inner vaginal tissue 21 and, without passing into or through vaginal tissue 25, to produce a deformation 29 in vaginal tissue 25 that is identifiable at outer vaginal tissue 23. Deformation 29 of outer vaginal tissue 23 can be identified through a leaf 10a or 10b. A fastener such as a grommet 27 (alternately a suture, staple, adhesive, or the like) may be placed over leaf 10a, 10b at deformation 29 to maintain the position of leaf 10a or 10b against the vaginal tissue 25. Fastener 27 may function to hold leaf 10a or 10b of Y-sling 10 in place while a more permanent attachment means or fastener is placed to secure leaf 10a or 10b at the surface of outer vaginal tissue 23. Once the Y-sling 10 is attached to the vaginal apex, extensions 25 can be optionally retracted, grommet 27 or alternate fastener can optionally be removed, and dilator 20b can be removed. The steps of attaching and detaching grommet 27 or another fastener to leaf 10a, 10b at deformation 29 may be performed laparoscopically or through an abdominal incision.

Figure 16A:
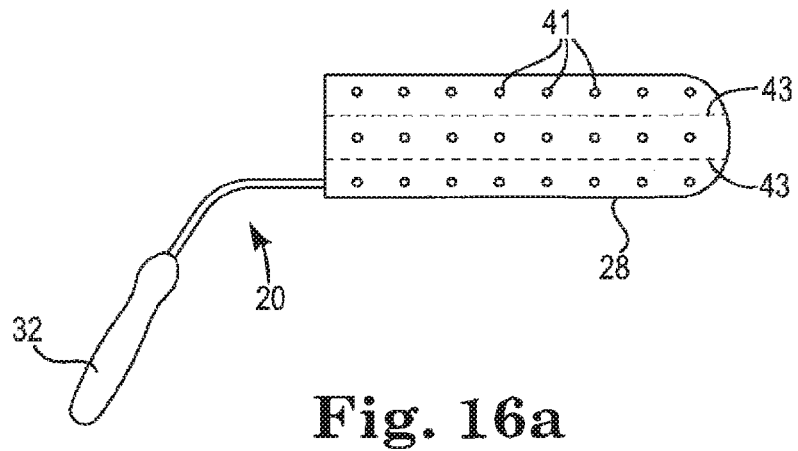
FIGS. 16a, 16b, and 16c, show alternative embodiments of dilators.
Figure 16B:
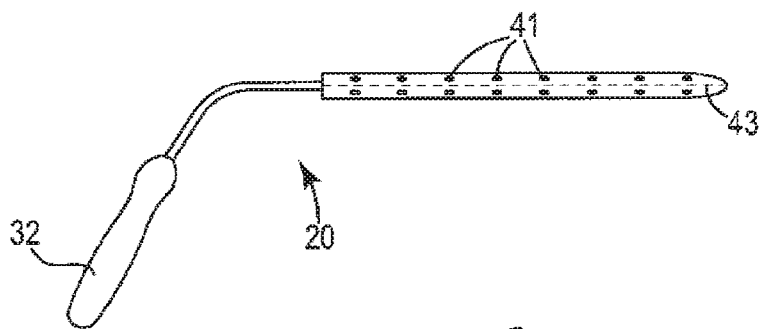
Figure 16C:
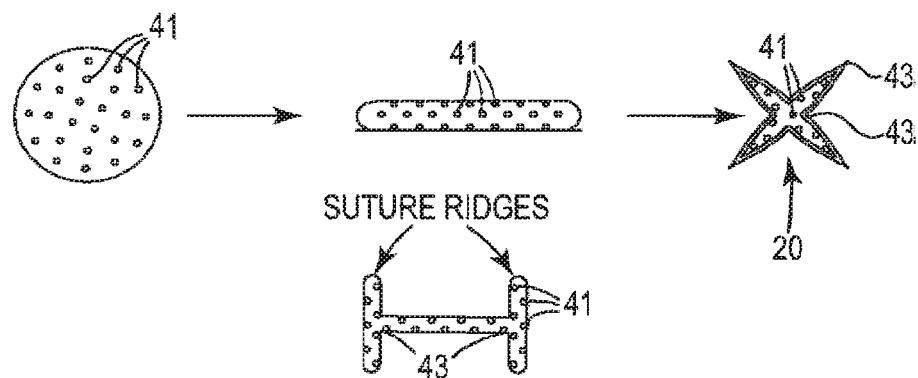

FIGS. 16a, 16b, and 16c illustrate embodiments of a dilator 20 that includes optional features that include vacuum ports 41 (to improve contact between dilator 20 and a surface of inner vaginal tissue 21) and fold lines 43. A dilator 20 may have a handle 32, shaft 36 and expansion portion 28 at a distal end as shown in FIG. 16a. The expansion portions 28 of the dilator 20 is the portion that is placed within a vagina during a sacral colpopexy procedure; according to FIGS. 16a, 16b, and 16c, as illustrated, dilator 20 may be expanded and contracted within a vagina during such a procedure, i.e., may have means for expansion and contraction such as vacuum ports, liquid balloon (not specifically shown), or other means. The expansion portion 28 may have pre-determined fold lines 43 for contraction. Upon contraction (e.g., by deflation), the dilator 20 (in end view) takes on a slender shape (as shown at FIG. 16b). Upon expansion (e.g., by inflation using a liquid or gaseous fluid), the dilator 20 (in end view) takes on an expanded shape such as a cylinder, rectangle, star, "H-shape," or other similar shape; some (four) examples of shapes (in end view) of an expanded dilator 20 are shown at FIG. 16c. Dilator 20 may also have an alignment mechanism 22 in the form of a ridge to guide placement of a fastener.

Figure 17A:
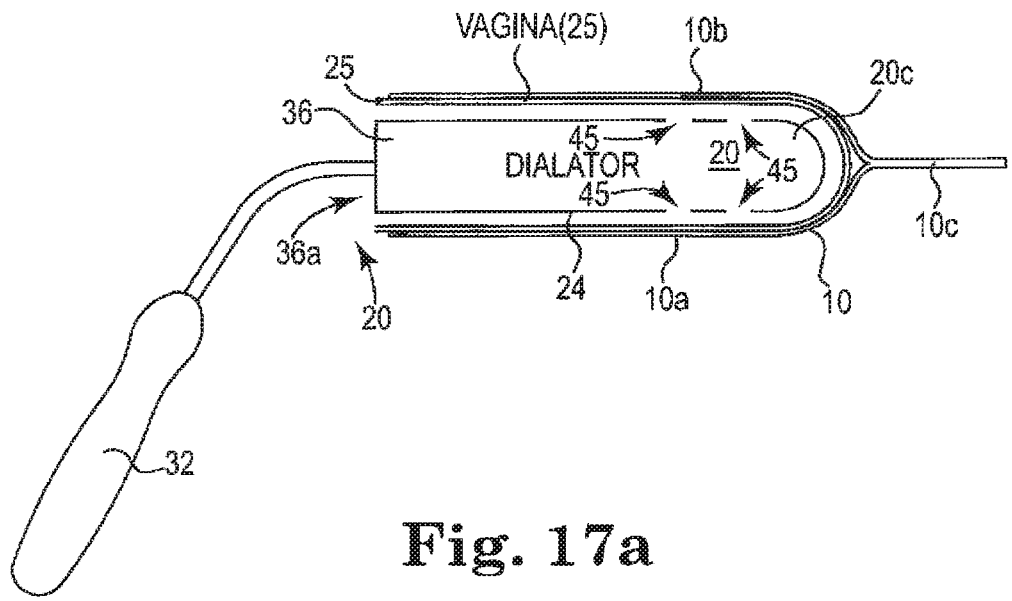
FIGS. 17a and 17b show alternative embodiments of dilators.
Figure 17B:
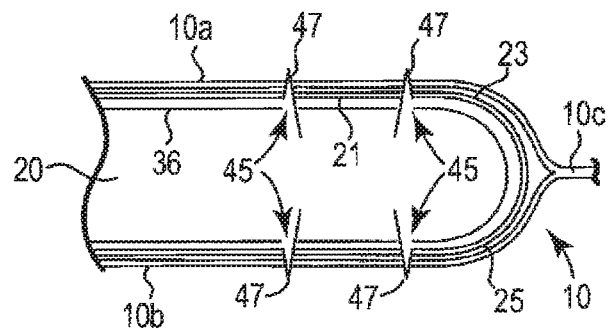

Alternately, a dilator 20 may have a hollow shaft 36 as in FIGS. 17a and 17b, the hollow interior of which may be accessed from the exterior of the patient while the hollow distal end of dilator 20 is inserted in a patient's vagina. The hollow shaft 36 of the dilator 20 includes a proximal opening 36a which is open to a proximal location exterior to a patient. Hollow shaft 36 also includes one or more access openings 46 at a distal end, at a location of vaginal tissue that is adjacent to and anterior to and posterior to the vaginal cuff. These access openings 45 provide for a surgeon to access vaginal tissue from a location within the hollow interior of dilator 20, using proximal opening 36a; the access can allow, for example, for a suture passer and suture to be passed through the vaginal wall 25 and also to be passed through an implant mesh (e.g., leaf 10a, 10b) located to contact outer vaginal tissue 23; the suture passer (e.g., needle) can be manipulated from within a hollow interior of shaft 36, optionally also from an external location of vaginal tissue 25 at a location of leaf 10a or 10b, e.g., laparoscopically or through an abdominal incision. By manipulating a suture passer (e.g., needle) and suture through access openings 45 and on the external location of vaginal tissue 25, a surgeon may place one or more suture in vaginal tissue 25 and through leaf 10a, 10b, to secure leaf 10a, 10b to vaginal tissue 25. The suture may be bioabsorbable or may be cut and removed at a time after the surgery from the interior side of the vagina to prevent aggravation of the vaginal mucosa. FIG. 17b additionally shows suture passers (e.g., needles) 47 extending from an interior of hollow shaft 36, through access openings 45, through vaginal tissue 24, and through leaf 10a, 10b, in a manner that allows formation of a suture knot to secure leaf 10a, 10b to vaginal tissue 25, followed by removal of suture passer 47 from the patient, e.g., through proximal opening 36a, and subsequent removal of dilator 20 and hollow shaft 36 from the patient.

Figure 18:
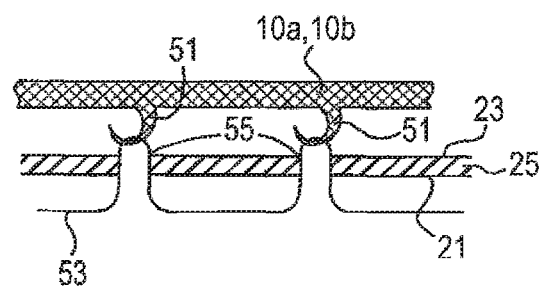
FIG. 18 shows an embodiment of a method of an implant material to tissue.

FIG. 18 shows a suture arrangement that may be achieved by use of a dilator 20 as shown at FIGS. 17a and 17b, the dilator 20 having one or more access openings 45 along a length of hollow shaft 36. A leaf 10a, 10b of Y-sling 10 may have barbs or hooks 51 that may be aligned with the access openings 45 and may engage a single or multiple loops of one or more suture passed through one or more opening 45, and also passed through adjacent vaginal tissue 25. The suture 53 may be passed through the vaginal wall 25 to form one or multiple loops 55, which can engage one or more hook 51. After placement of suture 53 and leaf 10a, 10b as shown at FIG. 18, the suture passer and dilator 20 (including hollow shaft 36) can be removed from the patient. Suture 53 may be bioabsorbable or may be removed at a desired time after surgery from the interior side of the vagina, to prevent aggravation of the vaginal mucosa.

Figure 19A:
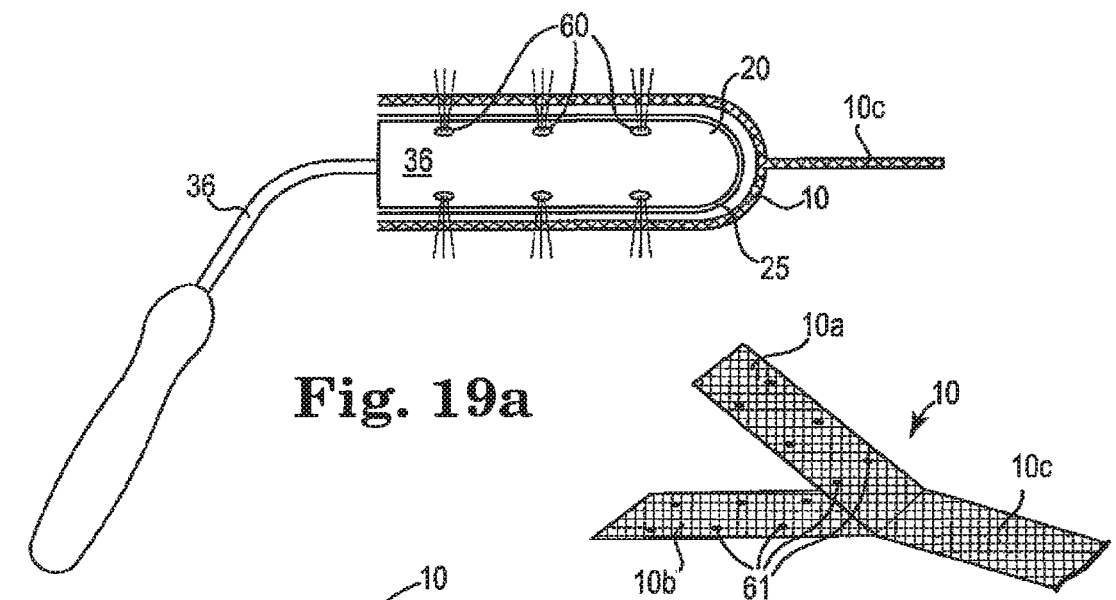
FIGS. 19a and 19b show an embodiment of a vaginal dilator and a Y-sling.

FIG. 19a illustrates a dilator 20 with a means for illumination 60 which may include any one or more of a light bulb (any type, including LED, LCD, incandescent, fluorescent, etc.), fiber optic material, a lens, etc, and (e.g., electronic) lighting control. The dilator shaft 36 may have one or more lighted openings 60 that can shine light toward vaginal tissue 25 at inner tissue 21 in a manner to illuminate the vaginal tissue with the light passing through the vaginal tissue and to the peritoneal cavity. The lighted vaginal tissue can facilitate correct placement and alignment of a Y-sling 10 (having any one or combination of features described herein) during laparoscopic or trans-abdominal (using an abdominal incision) placement and securing of Y-sling 10 and leafs 10a, 10b at vaginal tissue. Optionally, the dilator shaft 36 may be made from a translucent material that emits light along the entire shaft 36. Illumination could be a laparoscopic light or other light source fed through the dilator 20 such as a single fiber running through the middle of the dilator 20. Any of the dilators generally referenced or described herein can include a lighting feature, and any lighted dilator may be useful with any of the Y-slings described herein.

Figure 19B:
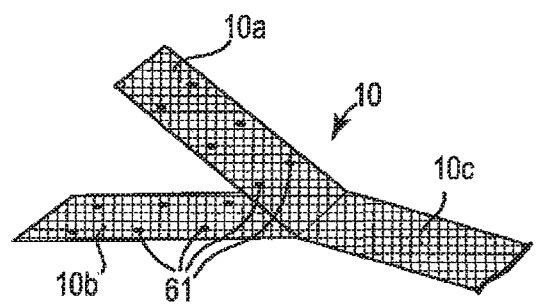

FIG. 19b shows Y-sling 10 that includes demarcations 61 at locations of a surface of one or more leaf 10a and 10b. These demarcations can correspond to locations for placing a fastener such as a staple or suture, laparoscopically, and their visibility may be enhanced by use of a dilator that includes means for illumination (e.g., 60) as described. In use for performing a sacral colpopexy, dilator 20 with means for illumination is inserted into a vagina and shines light through vaginal tissue 25. A Y-sling having demarcations 61 is inserted into the patient's abdomen, e.g., laparoscopically or via an abdominal incision. Leafs 10a and 10b are placed on outer vaginal surface 23 at anterior and posterior vaginal tissue near a vaginal cuff. Demarcations 61 are viewed, e.g., laparoscopically, and a suture, staple, or other fastener can be placed e.g., laparoscopically, at a location of one or more demarcations 61.

Figure 20A:
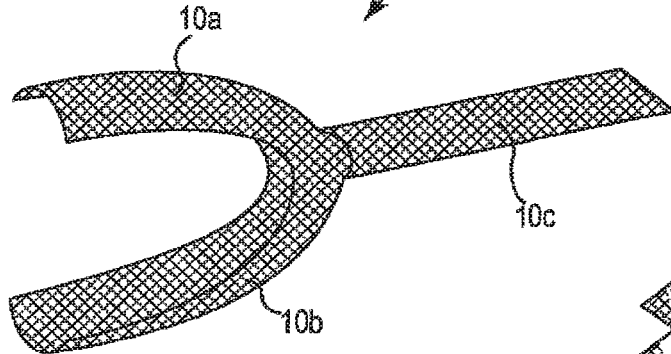
FIGS. 20a, 20b, 20c (detail) illustrate examples of Y-sling.

FIG. 20a shows a Y-sling 10 that is composed of a molded biocompatible material. The Y-sling 10 would be pre-molded to the shape of the vaginal apex to provide for better alignment and reduced bulk.

By certain exemplary methods of pre-molding a Y-sling, one or more portion of a Y-sling (e.g., one or more of leafs 10a, 10b, and 10c) may be treated to a stiffened, non-flat shape that corresponds to a shape of a vaginal apex, e.g., one leaf 10a corresponding to posterior vaginal tissue and one leaf 10b corresponding to anterior vaginal tissue. Treatment of a woven or knitted mesh material to be stiffened in this form may be by any desired method such as by thermo-forming, heat-treating, or by application of a polymeric or non-polymeric stiffening coating to the mesh material. The coating may be any biocompatible polymeric or non-polymeric coating material, and may be bioresorbable or non-bioresorbable. A stiffening coating can be applied using any suitable source and method to coat a portion of Y-sling for stiffening and shaping into a stiffened, biased, non-flat form. The coating may be a polymer that permanently stiffens surfaces or edges of the Y-sling. Alternately, the coating may be of a biocompatible or bioresorbable material that temporarily stiffens the material but is soluble and dissolves during chronic implantation. Suitable soluble materials (described, for example, in U.S. Pat. Nos. 4,827,940, 5,531,783 and 5,716,391) may be selected from among mannitol, dextrose, sorbose, sucrose, or salts, e.g., sodium chloride, potassium chloride, sodium carbonate, and polyvinylpyrrolidone (PVP).

Figure 20B:
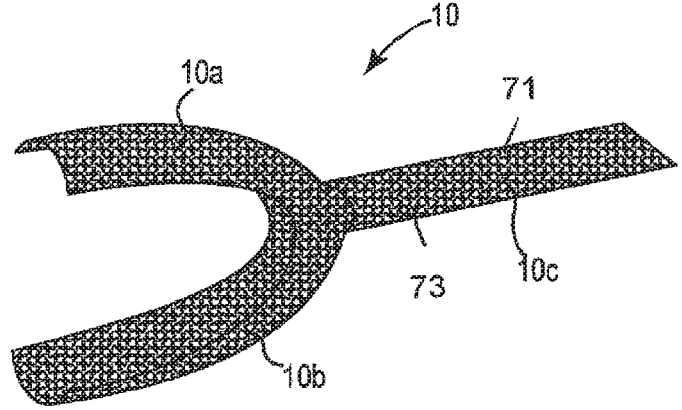
Figure 20C:
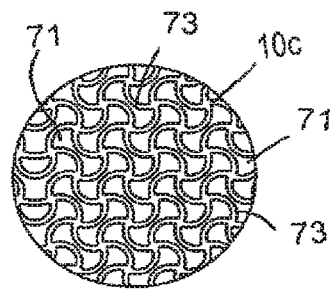

Another embodiment of a Y-sling useful as described herein is shown at FIGS. 20b and 20c, the illustrated Y-sling being a molded polymeric sling that is molded, e.g., injection molded, to a non-flat shape that corresponds to a shape of a vaginal apex, e.g., one leaf 10a corresponding to posterior vaginal tissue and one leaf 10b corresponding to anterior vaginal tissue.

The molded polymeric Y-sling may be prepared from a fenestrated polymeric film such as those described for use in various medical implant products in United States Patent applications 2011/0144417 and 2011/0124956, the entireties of which are incorporated herein by reference. See FIGS. 20b (perspective view) and 20c (detail of fenestrated structure).

In various embodiments, a molded polymeric Y-sling can be formed of an inelastic or elastic polymer, or an inelastic or elastic polymer having patterned fenestrations. The polymeric Y-sling may be prepared by any method, such as by molding (e.g., injection molding), 3-D printing, die casting, extrusion, or extrusion and laser etching, laser cutting, punching, and the like. Such a pattern-cut or formed polymeric Y-sling can be constructed of a polymer material to provide a lattice of repeated cells or fenestrations. Unlike woven or knitted conventional expandable Y-slings used in previous pelvic implant products, a molded polymeric Y-sling as described can be in the form of a homogeneous unitary construct.

A molded polymeric Y-sling can include a sacral leaf and two vaginal leafs, any of which may be fenestrated or non-fenestrated (solid) (see FIGS. 20b and 20c (detail of 10c)). According to certain embodiments the leafs include fenestrations formed by various lateral, longitudinal, diagonal, linear, non-linear, or otherwise oriented or shaped elastic or in-elastic sidewall structures (73). Fenestrations (71) may be of any geometry and may repeat a pattern of one or more shapes of the same size or different sizes. A fenestration may be round or rounded, circular, square, diamond-shaped, rectangular, triangular, or of any other regular or irregular shape (see FIG. 20c). The leaf structures are polymeric, non-woven and non-knitted, and may be elastic or inelastic. Each leaf may be of a uniform thickness along a length or width, or may be of a varying thickness along a length or with of the polymeric leaf, e.g., as produced using injection molding techniques. A thickness or material of one leaf may be different from a thickness or material of a different leaf; for example, thicker or stronger polymeric material may be used to prepare a sacral leaf (10c) of a Y-sling 10, and a less thick or less strong polymeric material may be used to prepare one or both of vaginal leafs 10a, 10b.

Figure 21:
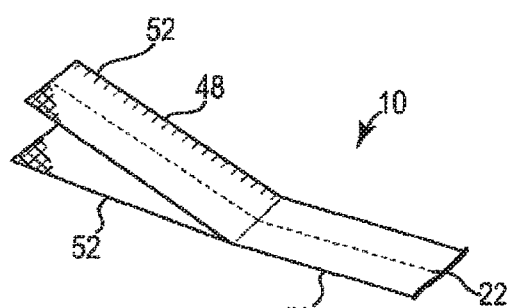
FIG. 21 shows an embodiment of a Y-sling.

FIG. 21 illustrates a Y-sling 10 useful for treating vaginal prolapse, including any of the various versions and embodiments of a Y-sling described herein having any one or more of the optional features also described. Y-sling 10 may have an alignment mechanism (e.g., demarcation, coloration) 22 located at about the longitudinal middle of the Y-sling 10. Y-sling 10 may also include hatch marks 48 on one or both of vaginal leafs 10a, 10b. Hatch marks 48 can aid is customization by guiding a physician where to cut the Y-sling 10. Y-sling 10 may be made of a synthetic mesh, biologic mesh, molded polymer, or other similar material. A higher density mesh or heavier material may be used on the extension portions 50 (sacral leaf) of Y-sling 10, and a lower density mesh or lighter material may be used on the support portions 52 (vaginal leafs 10a, 10b) of the Y-sling 10.

A Y-mesh implant, and dilator tool as described herein can include any one or more of the described features of the Y-mesh and dilator, in any combination, and any such Y-mesh and dilator may be used to perform a sacral colpopexy by any surgical method, including a laparoscopic method whereby the Y-mesh is introduced to a surgical site by way of a laparoscope and laparoscopic incision, while the dilator is placed inside of a patient's vagina to support the vaginal tissue. The method can also include placing a fastener, e.g., laparoscopically to secure the implant at vaginal anatomy and at a region of sacral anatomy. An implant that includes or is otherwise secured, adjusted, and manipulated as described might be useful to treat pelvic organ prolapse in a sacral colpopexy procedure performed trans-abdominally or laparoscopically, to provide support to vaginal tissue (e.g. a vaginal cuff), through an implant attached at the vaginal cuff and at a region of sacral anatomy such as a sacral ligament (e.g., anterior longitudinal ligament)

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but is also intended to encompass equivalents of those structures.

The invention claimed is:

1. A system for treating sacral colpopexy in a female patient, the system comprising a Y-sling implant, a dilator, and a fastening tool for fastening a vaginal leaf of the Y-sling implant to vaginal tissue, the fastening tool includes a handle, a shaft, a fastening mechanism, and a first magnet at a distal end of the shaft, the dilator includes a second magnet, the first magnet and the second magnet being configured to communicate to align the fastening tool with the dilator.

2. A system as recited at claim 1 wherein the dilator includes a distal end adapted to pass through a vaginal introitus to place the distal end within a vagina of the patient, and a proximal end that is configured to be disposed external to the patient when the distal end is placed within the vagina.

3. A system as recited at claim 2 wherein the distal end of the dilator includes a light.

4. A system as recited at claim 2 wherein the distal end of the dilator can be expanded and folded about a longitudinal axis.

5. A system as recited at claim 2 wherein the distal end of the dilator includes an alignment feature that can be identified through vaginal tissue with the distal end placed within the vagina.

6. A system as recited at claim 5 wherein the alignment feature is selected from a groove about a circumference of the distal end, a protrusion or ridge about a circumference of the distal end, a magnet, an extendable and retractable rod, a light, and combinations thereof.

7. A system as recited at claim 6 wherein the distal end of the dilator includes multiple openings in fluid communication with the proximal end, each opening adapted to contact a surface of interior vaginal tissue to expose the surface of interior vaginal tissue to a reduced pressure to maintain contact between the interior vaginal tissue and an outer surface of the distal end.

8. A system as recited at claim 7 wherein the Y-sling is capable of being reduced in cross section to a size that can be fit through a laparoscopic trocar.

9. A system as recited at claim 8 wherein the Y-sling includes a posterior vaginal leaf and an anterior vaginal leaf, and one or two of the leafs contain a frame.

10. A system as recited at claim 9 wherein the frame is selected from a nitinol coil, a polymeric elongate frame, a wound wire or elongate polymeric member extending lengthwise along the leaf, an elongate wire extending lengthwise along the leaf, and a curved wire or polymeric member.

11. A system as recited at claim 10 wherein the Y-sling includes a posterior vaginal leaf and an anterior vaginal leaf, and one or more of the leafs includes an adhesive.

12. A system as recited at claim 11 wherein the Y-sling includes a posterior vaginal leaf and an anterior vaginal leaf, and a connector extending between opposed edges of the vaginal leafs to connect the leafs.

13. A system as recited at claim 12 wherein the Y-sling includes a posterior vaginal leaf and an anterior vaginal leaf, and one or two of the leafs includes a fastener located on an inner surface, the fastener adapted to pass into vaginal tissue without passing through the vaginal tissue.

14. A system as recited at claim 13 wherein the Y-sling includes a posterior vaginal leaf and an anterior vaginal leaf, and one or more of the leafs includes a biological adhesive.

15. A system as recited at claim 14 wherein the Y-sling includes a posterior vaginal leaf and an anterior vaginal leaf, and one or more of the leafs includes a series of demarcations to indicate a location for placing a fastener to secure the leaf to vaginal tissue.

16. A system as recited at claim 15 comprising a tool for inserting the Y-sling laparoscopically, the tool comprising a handle, shaft, and a sheath, wherein the Y-sling can be contained within the sheath, the sheath is adapted to be passed laparoscopically into a pelvic region of the patient, and the Y-sling may be placed within the pelvic region by passing the Y-sling distally through an open distal end of the sheath.

17. A system as recited at claim 16 wherein the fastening mechanism is adapted to be passed laparoscopically into a pelvic region of the patient.

18. A system as recited at claim 17 wherein the first magnet and the second magnet are configured to communicate to place the fastening mechanism at a desired location to place a fastener.

19. A method of performing a sacral colpopexy, the method comprising
providing a system as recited at any of claims 1 through 18,
passing a distal end of the dilator through a vaginal introitus and positioning the distal end within a vagina of the patient, and using a proximal end to manipulate the distal end to support vaginal tissue,
passing a Y-sling into the patient through an abdominal incision or a laparoscopic incision to place the Y-sling at a location of outside vaginal tissue,
placing a vaginal leaf of the Y-sling at outside vaginal tissue and fastening the vaginal leaf to the vaginal tissue, and
fastening a sacral leaf of the Y-sling to tissue at a region of sacral anatomy.

\* \* \* \* \*